(12) United States Patent
Weslosky et al.

(10) Patent No.: US 11,385,141 B2
(45) Date of Patent: Jul. 12, 2022

(54) SAMPLING DEVICE FOR A MEDICAL WASHING DEVICE

(71) Applicant: Stryker Corporation, Kalamazoo, MI (US)

(72) Inventors: Michael Edward Weslosky, Kalamazoo, MI (US); Richard F. Huyser, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 39 days.

(21) Appl. No.: 16/834,208

(22) Filed: Mar. 30, 2020

(65) Prior Publication Data

US 2020/0225124 A1 Jul. 16, 2020

Related U.S. Application Data

(63) Continuation of application No. 15/388,025, filed on Dec. 22, 2016, now Pat. No. 10,620,093.

(60) Provisional application No. 62/387,199, filed on Dec. 23, 2015.

(51) Int. Cl.
*G01N 1/00* (2006.01)
*G01N 1/10* (2006.01)
*G01N 1/18* (2006.01)
*A61L 2/28* (2006.01)
*A61L 2/22* (2006.01)

(52) U.S. Cl.
CPC ............... *G01N 1/10* (2013.01); *A61L 2/22* (2013.01); *A61L 2/28* (2013.01); *G01N 1/18* (2013.01); *A61L 2202/17* (2013.01); *A61L 2202/24* (2013.01); *G01N 2001/185* (2013.01)

(58) Field of Classification Search
None
See application file for complete search history.

(56) References Cited

U.S. PATENT DOCUMENTS

| | | | |
|---|---|---|---|
| 2,734,306 A | 2/1956 | Holdeman | |
| 4,849,177 A | 7/1989 | Jordan | |
| 5,138,868 A * | 8/1992 | Long | G01N 35/1011 73/1.79 |
| 5,794,695 A | 8/1998 | Peterson | |
| 6,071,477 A | 6/2000 | Auclair et al. | |
| 7,687,028 B1 | 3/2010 | Coplen, II | |
| 10,088,460 B2 * | 10/2018 | DeWitte | G01N 30/7233 |
| 10,620,093 B2 | 4/2020 | Weslosky et al. | |
| 2011/0176963 A1 | 7/2011 | Kim et al. | |

(Continued)

OTHER PUBLICATIONS

"Variability of ATP amount in last rinse water of automated washer-disinfectors demands monitoring of every load", Journal of Hospital Infection, 91, 2015, pp. 87-92.

*Primary Examiner* — Jyoti Nagpaul
(74) *Attorney, Agent, or Firm* — Howard & Howard Attorneys PLLC

(57) ABSTRACT

A sampling device and associated methods for assessing operation of a medical washing device includes a base, a cover, a fluid path, a sensor, and a controller. The cover is selectively removably mounted to the base and includes an opening. The fluid path is in fluid communication with the opening, and has an outlet through which the fluid is discharged. The sensor is a sensor of an analytical characteristic, and is disposed in the fluid path. The controller is in communication with the sensors.

5 Claims, 16 Drawing Sheets

(56) References Cited

U.S. PATENT DOCUMENTS

2015/0153370 A1  6/2015  Saito et al.
2017/0183706 A1  6/2017  Weslosky et al.

* cited by examiner

SAMPLING DEVICE FOR A MEDICAL WASHING DEVICE

RELATED APPLICATIONS

This application is a continuation of U.S. patent application Ser. No. 15/388,025, filed Dec. 22, 2016, which claims priority to and the benefit of U.S. Provisional Patent Application No. 62/387,199, filed on Dec. 23, 2015, the entire contents of which are hereby incorporated by reference.

TECHNICAL FIELD

The present disclosure generally relates to a sampling device for collecting samples in a medical sterilization device. More specifically, the disclosure relates to the sampling device for collecting a plurality of samples of a solution in the medical sterilization device in a plurality of vessels, and to a method for collecting the plurality of samples of the solution in the medical sterilization device.

BACKGROUND

Hospitals and other health care related operations utilize medical sterilization devices for sterilizing and sanitizing medical instruments and devices that may be soiled. The medical sterilization device utilizes various solutions for sterilizing, lubricating, cleaning, and/or sanitizing the medical instruments and devices. During sterilization and sanitization in the medical sterilization device, the solution may become ineffective due to concentration of various solutes or the level of soil of the medical instruments. A user of the medical sterilization device has no ability to determine whether the medical sterilization device is performing effectively.

It is an object of the present disclosure to provide a new sampling device and a method for improved analysis of in the operation of the medical sterilization device.

SUMMARY

The present disclosure provides for a sampling device for collecting a plurality of samples of a solution in a medical sterilization device in a plurality of vessels. The plurality of vessels includes a first vessel and a second vessel. The sampling device includes a base configured to support the plurality of vessels, and a cover including an orifice. The cover and the plurality of vessels define an orientation in relation to each other. The orientation has a first position that permits ingress of the solution through the orifice into the first vessel and a second position that permits ingress of the solution through the orifice into the second vessel. The cover is configured to prevent ingress of the solution into the second vessel when the orientation is in the first position and the cover is configured to prevent ingress of the solution into the first vessel when the orientation is in the second position.

The present disclosure further provides a sampling device for collecting a plurality of samples of a solution in a medical sterilization device with the sampling device comprising a plurality of vessels comprising a first vessel and a second vessel. A base is configured to support the plurality of vessels within the medical sterilization device. The sampling device is deployable between a first configuration comprising permitting ingress of the solution into the first vessel and preventing ingress of the solution into the second vessel, and a second configuration comprising preventing ingress of the solution into the second vessel and permitting ingress of the solution into the first vessel.

A method of collecting the plurality of samples of the solution in the medical sterilization device is also provided. The method utilizes the sampling device described above. The cover and the plurality of vessels define an orientation in relation to each other. The method includes the step of positioning the sampling device in the medical sterilization device. The method also includes the step of changing the orientation of the cover relative to the plurality of vessels to the first position to permit ingress of the solution through the orifice into the first vessel and prevent ingress of the solution into the second vessel. The method further includes the step of collecting a first sample of the solution in the first vessel. The method also includes the step of changing the orientation of the cover relative to the plurality of vessels to the second position to permit ingress of the solution through the orifice into the second vessel and prevent ingress of the solution into the first vessel. The method further includes the step of collecting a second sample of the solution in the second vessel.

DETAILED DESCRIPTION

Figure 1:
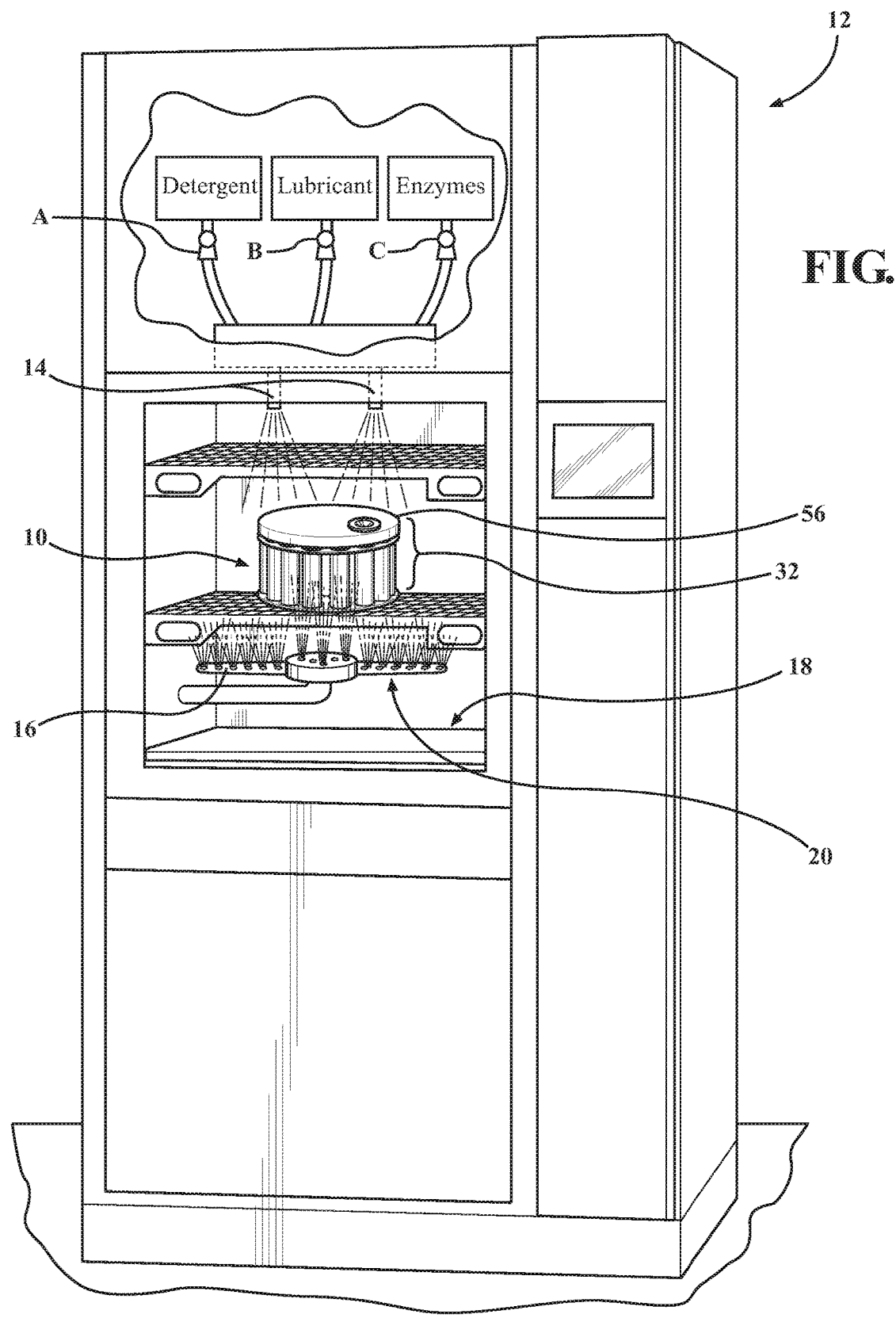
FIG. 1 is a perspective view of a medical sterilization device including a sampling device disposed therein.
Figure 10:
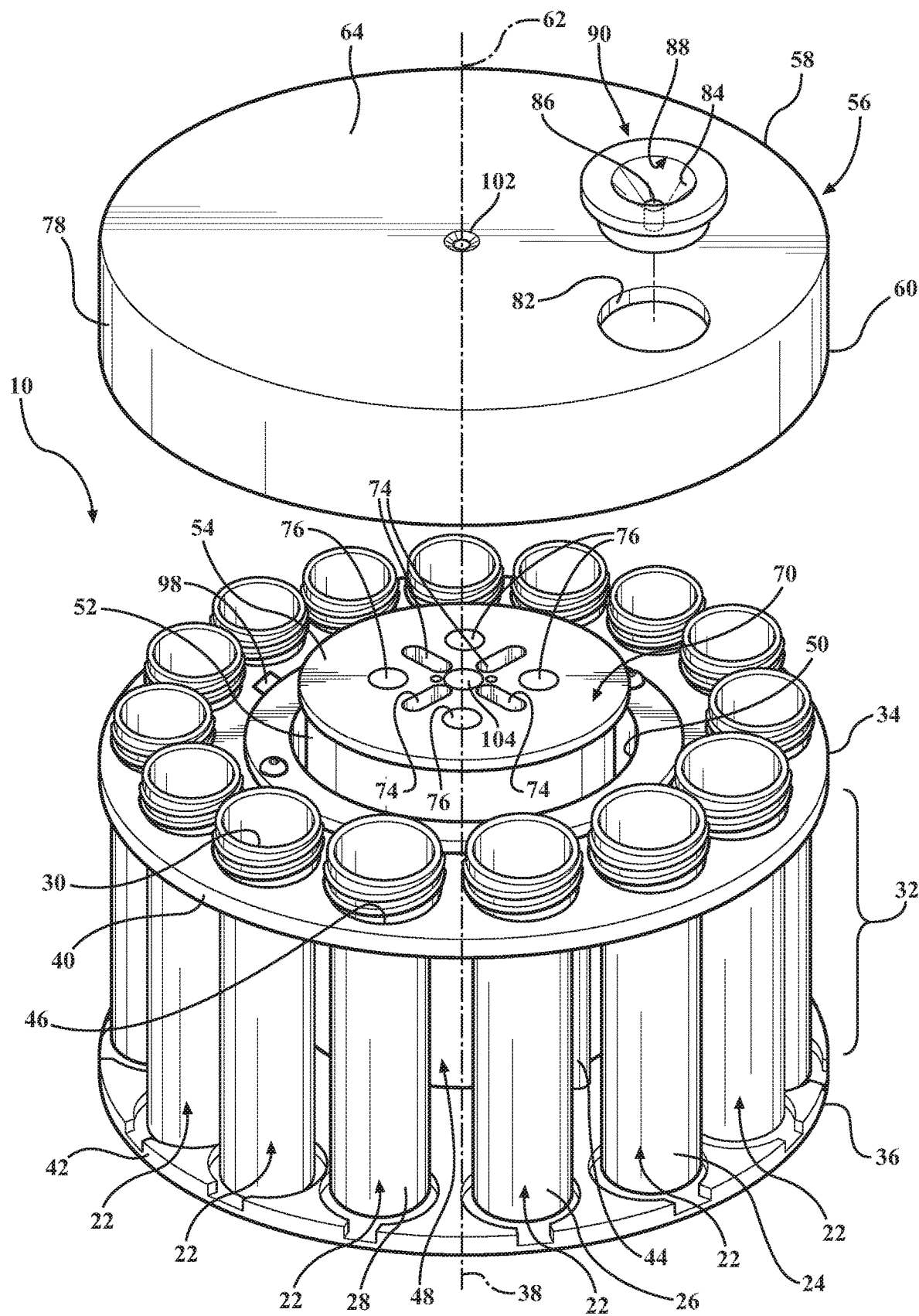
FIG. 10 is a perspective view of a sampling device in accordance with another exemplary embodiment with an opening in each of the cover and the base.

Referring to FIG. 1, the present disclosure provides a sampling device 10 for collecting a plurality of samples of a solution in a medical sterilization device 12. Referring to FIG. 10, the present disclosure also provides a method for collecting the plurality of samples of the solution in the medical sterilization device 12. The method utilizes the sampling device 10.

The medical sterilization device 12 may include fluid sources 14, 16, such as an external fluid source 14 and an internal fluid source 16, for introducing the solution into a tub 18 of the medical sterilization device 12. Further types of fluid output by external and internal fluid sources are not particularly limited. The medical sterilization device 12 may further include a rotary spray arm 20 for recirculating the solution in the tub 18. The solution that is circulated in the tub 18 may be further defined as one or more circulated solutions. In certain embodiments, the rotary spray arm 20 includes the internal fluid source 14. The medical sterilization device 12 may further include one or more injection pumps A, B, C fluidly coupled to the external fluid source 14 for moving the solutions to the external fluid source 14.

The medical sterilization device 12 may include one or more cycles for introducing the solution into the tub 18 and recirculating the solution in the tub 18, such as a pre-wash cycle, an enzyme cycle, a wash cycle, a rinse cycle, a lubricant cycle, a thermal rinse cycle, a drying cycle, or combinations thereof. However, it is to be appreciated that the medical sterilization device 12 may include additional cycles. It should also be appreciated that the sampling device 10 may be used in any application where fluid sampling is required.

During use of the medical sterilization device 12, one or more cycles of the medical sterilization device 12 are initiated such that the solution is circulated in the tub 18 from the fluid sources 14, 16 to the tub 18. Once the cycles are complete, the sampling device 10 may be removed from the tub 18 of the medical sterilization device 12. It is also to be contemplated that the sampling device 10 may be removed from the tub 18 during the cycle of the medical sterilization device 12.

The solution of the medical sterilization device 12, output by the external fluid source 14 and the internal fluid source 16 of the rotary spray arm 20, may be utilized for sterilizing, lubricating, cleaning, and sanitizing medical instruments and devices. The solution may include detergent solutions, lubricant solutions, enzyme solutions (e.g. an enzymatic detergent), or combinations thereof. Of course, other types of solutions may also be introduced into the tub 18 through the external fluid source 14 to yield other desirable effects. Each of the cycles of the medical sterilization device 12 may introduce and recirculate one or more of the solutions. For example, during the wash cycle, the detergent solution may be introduced into the tub 18 by the external fluid source 14 and both the detergent solution and the enzyme solution may be recirculated in the tub 18 by the internal fluid source 16 of the rotary spray arm 20.

The solutions described above may be formed from a mixture of an additive and a solvent. For example, the detergent solution may be formed from a detergent additive and water; the lubricant solution may be formed from a lubricant additive and water; and the enzyme solution may be formed from an enzyme additive and water. Of course, any number of additives or solvents may be utilized. In certain embodiments, one injection pump of the medical sterilization device 12 combines the detergent additive with the solvent, and transports the detergent solution to the external fluid sources 14, another injection pump combines the lubricant additive with the solvent, and transports the lubricant solution to the external fluid sources 14, and so forth. It is to be appreciated that the additives may be combined with the solvent after being introduced into the tub 18.

The tub 18 of the medical sterilization device 12 is configured to accommodate one or more devices that need to be sterilized. The sampling device 10 is disposed in the tub 18 to permit contact of the solution provided by the fluid sources 14, 16 with the sampling device 10. Thus, the sampling device 10 may be in contact with circulated fluids that are present within the tub 18 including fluid provided by the internal fluid source 16, the external fluid source 14, or the circulated solutions. Additionally, the sampling device 10 may be present during any combination of cycles. In certain embodiments, the sampling device 10 is positioned in the center of the tub 18.

Figure 2:
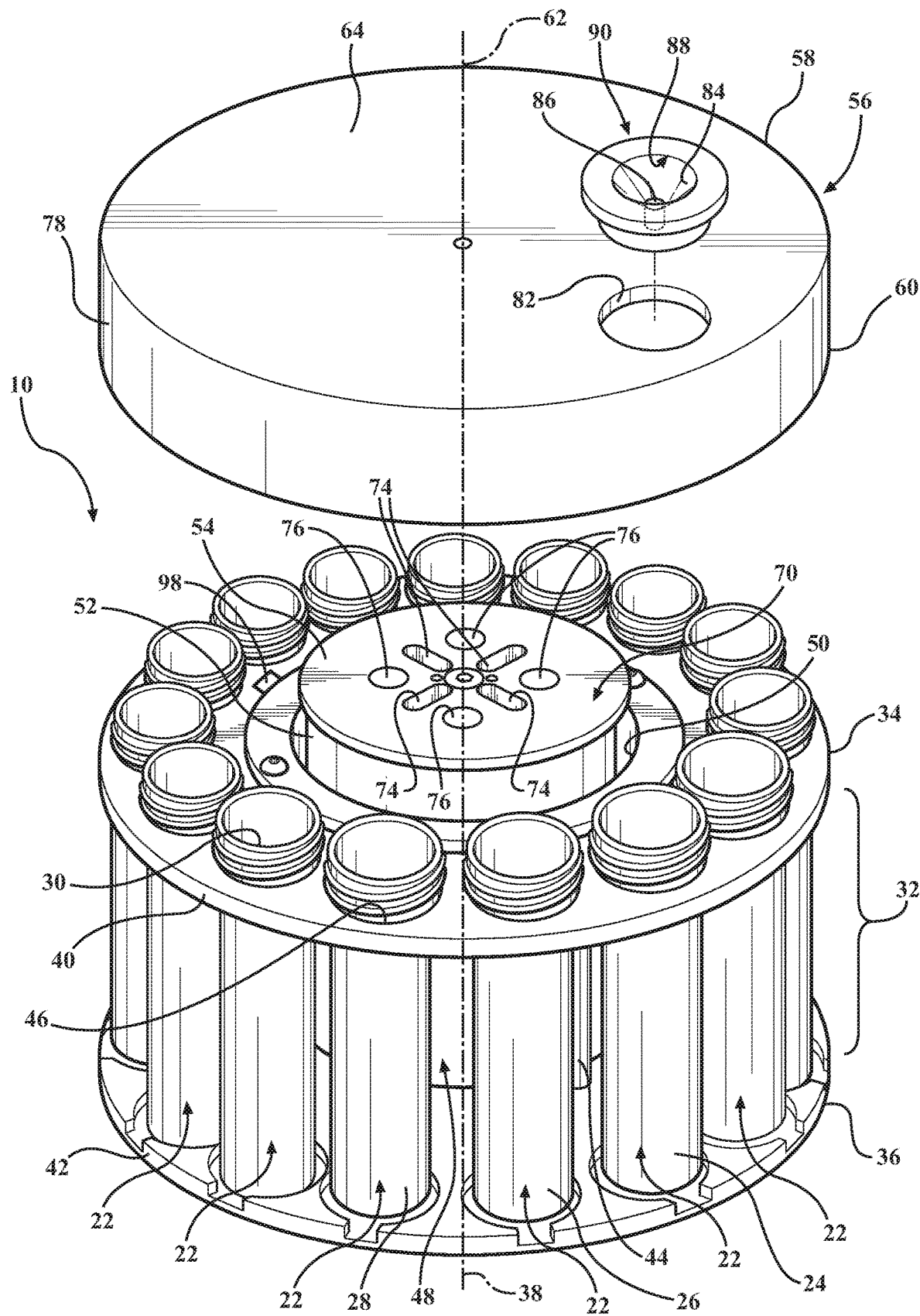
FIG. 2 is a perspective view of the sampling device of FIG. 1 including a cover and a base with the cover spaced from the base.

Referring to FIG. 2, in one exemplary embodiment the sampling device 10 includes a plurality of vessels 22 with the vessels 22 including a first vessel 24 and a second vessel 26. The vessels 22 may further include a third vessel 28. In one embodiment, the vessels 22 includes fifteen vessels. The vessels 22 may be formed of any suitable material so long as the vessels 22 are capable of collecting the solution and withstanding the conditions, such as the temperature and corrosivity, of the medical sterilization device 12 without melting or degrading. In certain embodiments, the vessels 22 are formed from polypropylene. Each of the vessels 22 may be configured to collect the solution in an amount of from 10 to 100 ml. Of course, any suitable size vessel may be utilized in the sampling device 10. Each of the vessels 22 includes an opening 30 for permitting ingress of the solution into each of the vessels 22. The opening 30 may be shaped or configured in various ways to suitably channel fluid into the vessels 22. For example, each opening 30 has a circular shape. The vessels 22 may have a bottom which is flat and opposite the opening 30.

Figure 4:
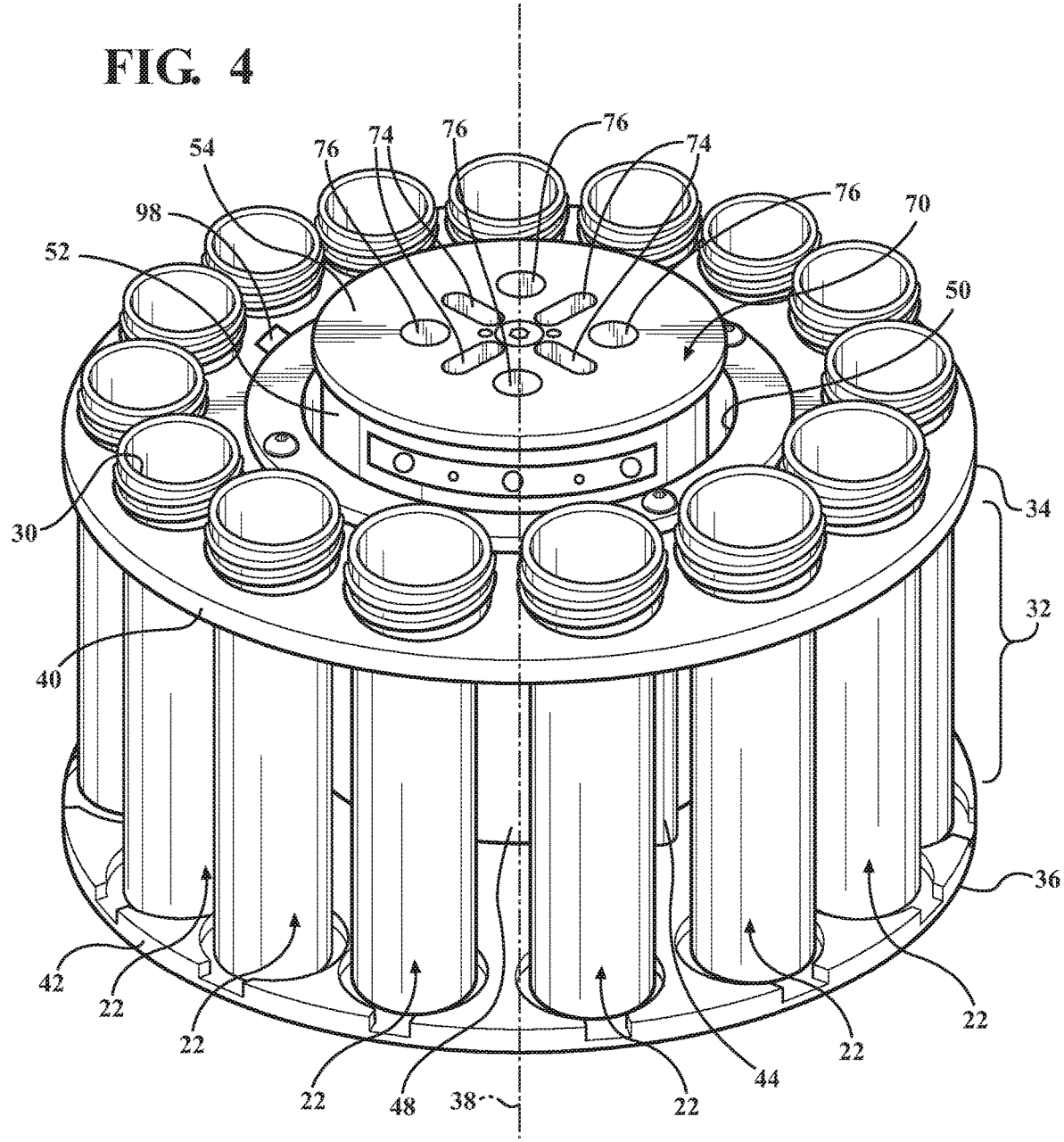
FIG. 4 is a perspective view of the sampling device of FIG. 1 with the cover

Referring to FIG. 4, the sampling device 10 includes a base 32 configured to support and/or removably retain the vessels 22. In certain embodiments, the base 32 has a generally cylindrical shape. However, it is to be appreciated that the base 32 may have any suitable shape, such as a rectangular shape. In various embodiments, the base 32 has a top end 34 and a bottom end 36 with a first longitudinal axis 38 extending therebetween. The base 32 may include a rack 40 adjacent to the top end 34 and a floor 42 adjacent to the bottom end 36. The base 32 may further include one or more pillars 44 disposed between the rack 40 and the floor 42. One end of the pillar 44 may be coupled to the floor 42 and the other end of the pillar 44 may be coupled to the rack 40 such that the floor 42 is coupled to the rack 40. The base 32 may extend transverse to the first longitudinal axis 38 to a first perimeter. More specifically, both of the rack 40 and the floor 42 may extend transverse to the first longitudinal axis 38 to the first perimeter. The floor 42 of the base 32 may be disposed on a shelf of the tub 18 of the medical sterilization device 12.

The rack 40 may be configured to removably retain the vessels 22. The rack 40 may define a plurality of slots 46 with each of the slots 46 configured to accommodate one of the vessels 22. The rack 40 may be formed of any material so long as the rack 40 can removably retain the vessels 22.

In various embodiments, when the vessels 22 are disposed in the rack 40, the openings 30 of the vessels 22 are disposed adjacent the top end 34 of the base 32.

The base 32 may further include a motor 48. The motor 48 may be disposed between the top end 34 and the bottom end 36 of the base 32. In certain embodiments, the rack 40 and the floor 42 define an aperture 50 along the first longitudinal axis 38 of the base 32 with the motor 48 disposed in the aperture 50. The motor 48 includes a housing 52, a rotor, and a head 54 with the rotor coupling the housing 52 to the head 54 and rotatable about the housing 52. The rotor of the motor 48 may rotate the head 54 about the first longitudinal axis 38 of the base 32.

Referring again to FIG. 2, the sampling device 10 further includes a cover 56. In certain embodiments, the cover 56 has a generally cylindrical shape. However, it is to be appreciated that the cover 56 may have any shape, such as a rectangular shape. The cover 56 may be formed of any material withstanding the conditions of the medical sterilization device 12. In various embodiments, the cover 56 has an upper end 58 and a lower end 60 with a second longitudinal axis 62 extending therebetween. The cover 56 may extend transverse to the second longitudinal axis 62 to a second perimeter. The cover 56 may include a top surface 64 extending from the second longitudinal axis 62 to the second perimeter and a bottom surface 66 opposite the top surface 64. In various embodiments, the base 32 and the cover 56 are configured such that the first perimeter of the base 32 and the second perimeter of the cover 56 have a similar size. However, it is to be appreciated that the second perimeter of the cover 56 may extend beyond the first perimeter of the base 32 or the first perimeter of the base 32 may extend beyond the second perimeter of the cover 56.

In certain embodiments, the cover 56 is removably coupled to the sampling device 10 adjacent the top end 34 of base 32. In one embodiment, the cover 56 is removably coupled to the motor 48 of the base 32. The first longitudinal axis 38 of the base 32 and the second longitudinal axis 62 of the cover 56 may be inline with each other when the cover 56 is coupled to the sampling device 10. In other embodiments, the cover 56 is integral with the base 32.

Figure 5:
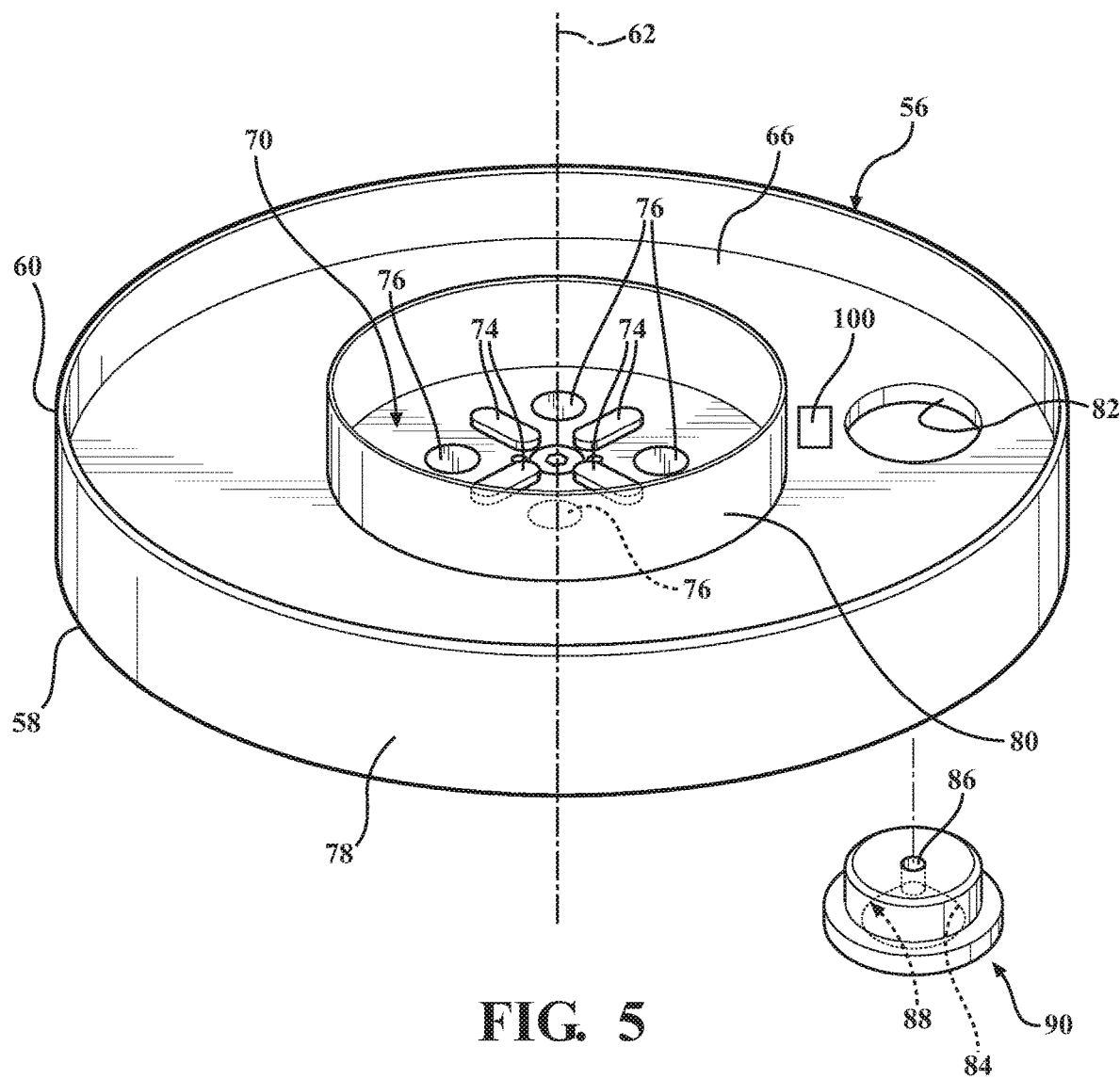
FIG. 5 is a perspective view of a bottom surface of the cover of the sampling device.
Figure 6:
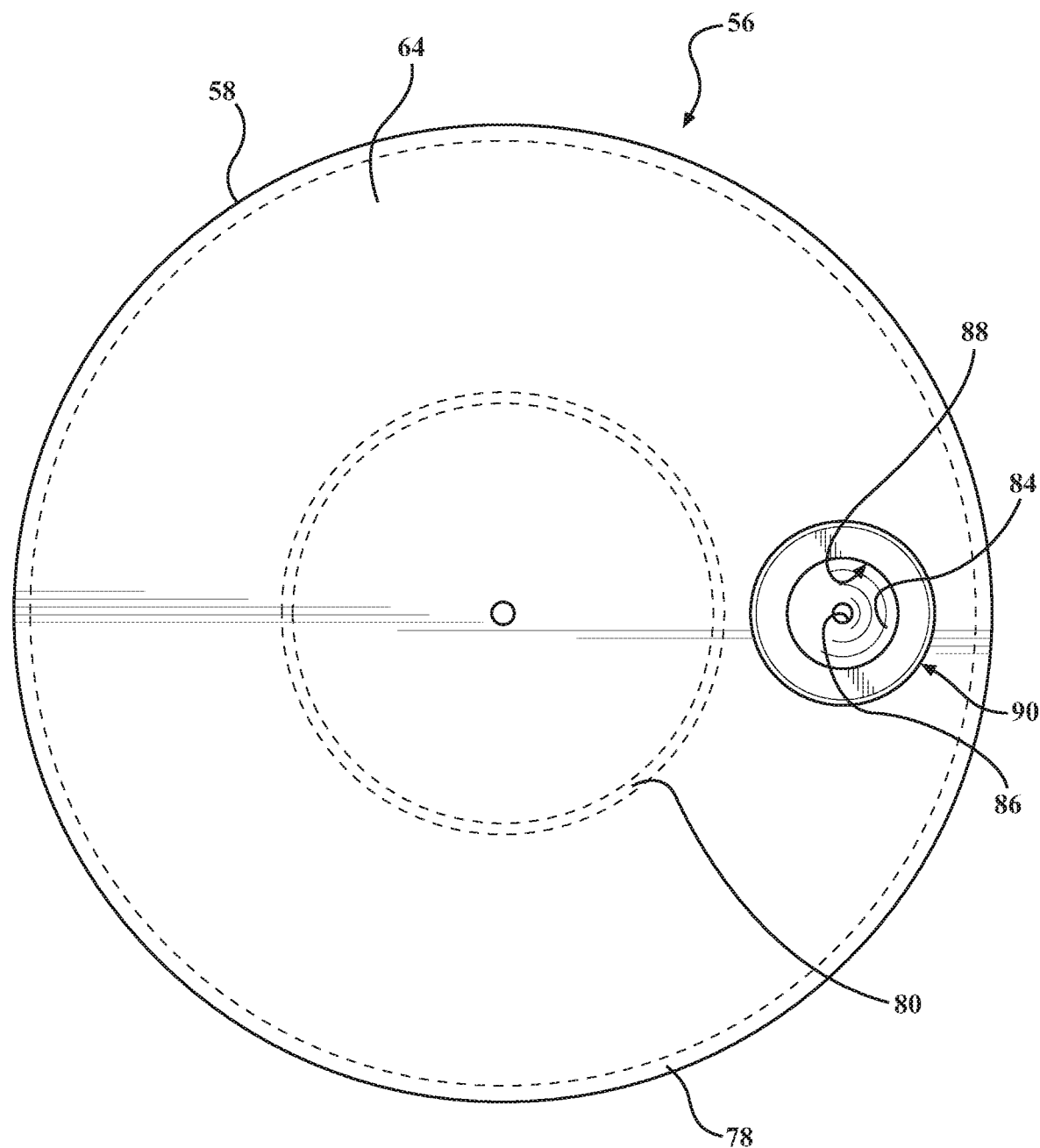
FIG. 6 is a top plan view of the cover of the sampling device.

Referring to FIGS. 4 and 5, in certain embodiments, the sampling device 10 further includes a coupling mechanism 70 configured to removably couple the cover 56 to the motor 48. The coupling mechanism 70 may include one or more extensions 72 disposed on the bottom surface 66 of the cover 56. The coupling mechanism 70 may further include one or more recesses 74 defined in the head 54 of the motor 48. The extensions 72 may be configured to engage the recesses 74 such that when the cover 56 is coupled to the motor 48, the engagement of the extensions 72 and the recesses 74 prevents rotational movement between the cover 56 and the head 54 of the motor 48. The coupling mechanism 70 may further include one or more magnets 76 disposed on the bottom surface 66 of the cover 56 and on the head 54 of the motor 48. The magnets 76 disposed on the bottom surface 66 of the cover 56 may oppose the magnets 76 disposed on the head 54 of the motor 48 such that when the cover 56 is coupled to the motor 48, the magnetic force of attraction of each set of opposing magnets biases the cover 56 to the head 54 of the motor 48. It is to be appreciated that the cover 56 may be coupled to the motor 48 by any manner known in the art, such as by a fastener, adhesive, a tongue and groove joint, etc.

Referring to FIG. 5, the cover 56 may include a vessel shielding portion 78 disposed at the second perimeter of the cover 56 and extending from the upper end 58 to the lower end 60 of the cover 56. The vessel shielding portion 78 may be configured to prevent contact between the solution and the openings 30 of the vessels 22 such that the cover 56 is configured to prevent unwanted ingress of the solution into the vessels 22. In certain embodiments, the vessel shielding portion 78 is configured to engage the rack 40 of the base 32 to prevent contact between the solution and the openings 30 of the vessels 22 that could occur if the solution was directed at the side of the sampling device 10.

The cover 56 may further include a motor shielding portion 80 configured to prevent contact between the solution and the motor 48. When the cover 56 is coupled to the motor 48, the motor shielding portion 80 may extend from the cover 56 to the base 32 and about a periphery of the motor 48. In certain embodiments, the motor shielding portion 80 is configured to engage the rack 40 of the base 32 to prevent contact between the solution and the motor 48.

Referring to FIGS. 3A-3C and 6, the cover 56 includes an orifice 82. In certain embodiments, the top surface 64 of the cover 56 includes or defines the orifice 82. The orifice 82 may have a diameter of from 1 to 20 mm. However, it is to be appreciated that the diameter of the orifice 82 may be any suitable diameter for the sampling device 10. The orifice 82 permits the solution from the fluid sources 14, 16 of the medical sterilization device 12 to pass through the cover 56 and into the vessels 22. In certain embodiments, the orifice 82 permits ingress of the solution to the vessels 22.

The cover 56 may include an insert 90 disposed in the orifice 82 with the insert 90 defining a hole 88. In embodiments when the cover 56 defines the orifice 82 with the insert 90 disposed therein, the hole 88 may define the orifice 82 of the cover 56. The insert 90 may define an outer portion 84 of the hole 88 and an inner portion 86 of the hole 88 with the outer portion 84 and the inner portion 86 in fluid communication with each other. It is to be appreciated that the cover 56 may define with the outer portion 84 and the inner portion 86 of the hole 88. In certain embodiments, the hole 88 has a funnel-like configuration to direct the solution from the fluid sources 14, 16 of the medical sterilization device 12 to the vessels 22. When the cover 56 is coupled to the sampling device 10, the inner portion 86 is adjacent the base 32 and the outer portion 84 is opposite the base 32. The outer portion 84 of the hole 88 may have a diameter of from 5 to 20 mm. The inner portion 86 of the hole 88 may have a diameter of from 1 to 5 mm. However, it is to be appreciated that the diameter of the outer portion 84 and the inner portion 86 of the hole 88 may be any suitable diameter for the sampling device 10. The dimensions of the insert 90 are not particularly limited, and may be tailored to the flow rate desired. The insert 90 may be formed of any material withstanding the conditions of the medical sterilization device 12. In one embodiment, the insert 90 is formed from a UV curable polymer. In certain embodiments, the insert 90 has a generally cylindrical configuration. However, it is to be appreciated that the insert 90 may have any configuration, such as a rectangular configuration. In certain embodiments, the insert 90 is not disposed in the hole 88. In these embodiments, the hole 88 may be sufficiently contoured to direct the solution from the fluid sources 14, 16 of the medical sterilization device 12 to the vessels 22.

In various embodiments, the openings 30 of the vessels 22 face the cover 56 such that the orifice 82 directs the solution from the fluid sources 14, 16 to one or more of the openings 30. More specifically, the solution from the fluid sources 14, 16 may contact the outer portion 84 of the hole 88, move from the outer portion 84 to the inner portion 86 of the hole 88, move from the inner portion 86 to the openings 30 of the vessels 22, and collect in one or more of the vessels 22. It is to be appreciated that the cover 56 may include more than one orifice, such as a second orifice. In one embodiment, the second orifice directs the solution to the opening 30 of the same vessel as the orifice 82 directs the solution to. In another embodiment, the second orifice directs the solution to the opening 30 of a different vessel than the orifice 82 directs the solution to.

The sampling device 10 may be configured to enable gravity to transfer the solution from the orifice 82 to the vessels 22. The solution from the fluid sources 14, 16 may contact the outer portion 84 of the hole 88, move via the force of gravity from the outer portion 84 to the inner portion 86 of the hole 88, and move via the force of gravity from the inner portion 86 to the openings 30 of the vessels 22. In various embodiments, the sampling device 10 is free of a pump.

As introduced above, the samples of the solution are collected in the vessels 22. In certain embodiments, the samples of the solution includes a first sample and a second sample. However, it is to be appreciated that the samples may include a third sample. In one embodiment, the samples includes fifteen samples. The first sample of solution may be collected in the first vessel 24. The second sample of solution may be collected in the second vessel 26. The third sample of solution may be collected in the third vessel 28.

The cover 56 and the vessels 22 define orientations in relation to each other. The orientations may include first position and a second position of the cover 56. However, it is to be appreciated that the orientations may include more than two positions, such as a third position, with each of the positions of the cover 56 corresponding to one of the vessels 22. The illustrated embodiment includes orientations having fifteen positions. The orientation may be changed to the first position, the second position, the third position, etc. In certain embodiments, the sampling device 10 is movable to the first position and the second position.

Figure 3A:
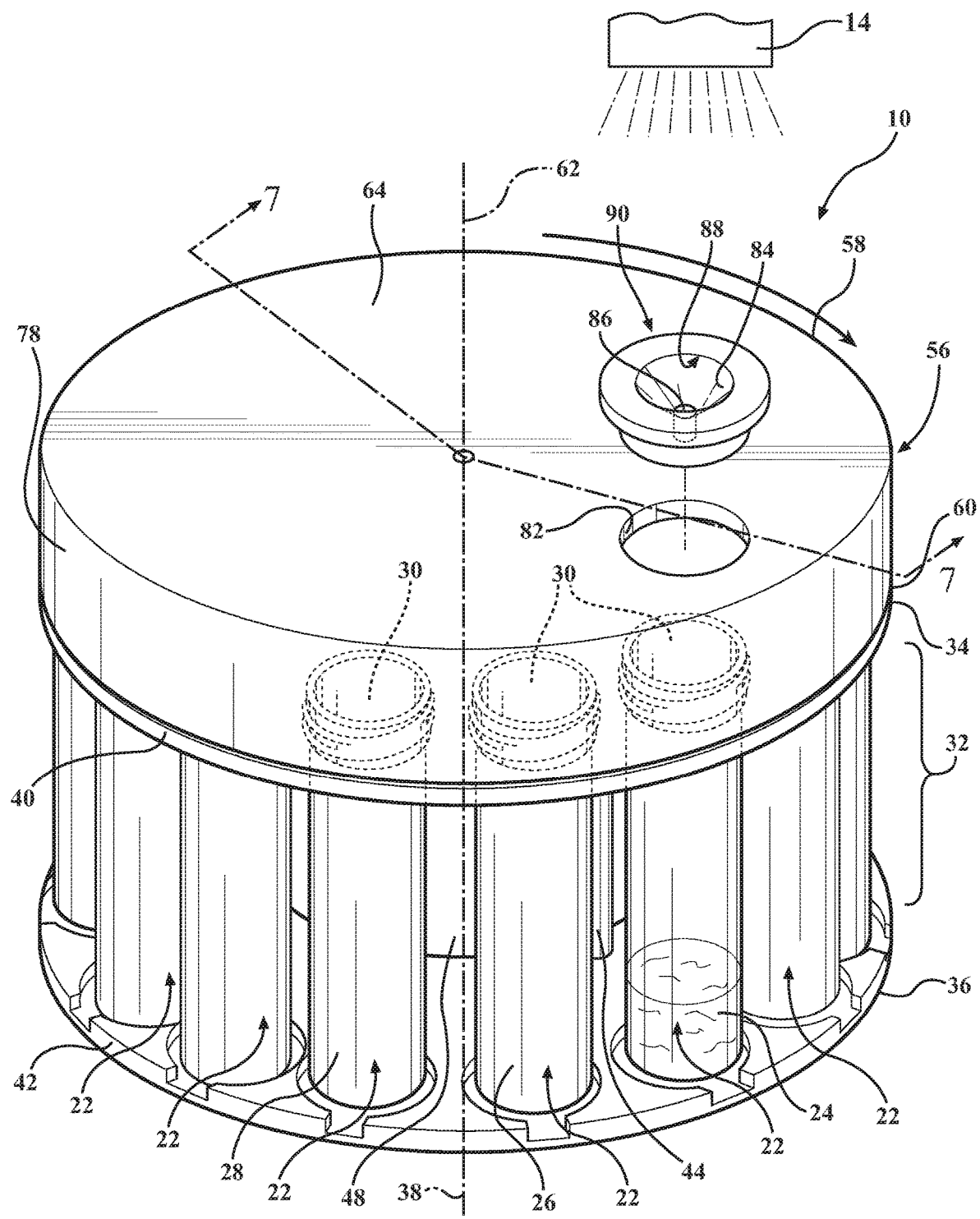
FIG. 3A is a perspective view of the sampling device in a first position.

Referring to FIG. 3A, the first position of the orientation of the sampling device 10 permits ingress of the solution through the orifice 82 into the first vessel 24. Thus, the orifice 82 permits fluid communication from the fluid sources 14, 16 to the first vessel 24 when the orientation is in the first position. More specifically, when the orientation is in the first position, the solution from the fluid sources 14, 16 may contact the outer portion 84 of the hole 88, move from the outer portion 84 to the inner portion 86 of the hole 88, move from the inner portion 86 to the opening 30 of the first vessel 24, and collect in the first vessel 24. In certain embodiments, the inner portion 86 of the hole 88 is inline with the opening 30 of the first vessel 24 such that the solution moves via gravity from the inner portion 86 to the opening 30 of the first vessel 24 when the orientation is in the first position.

When the orientation is in the first position, the orientation is configured to prevent ingress of the solution into the second vessel 26. In embodiments when the sampling device 10 includes additional vessels beyond the first vessel 24 and the second vessel 26, the cover 56 may be configured to prevent ingress of the solution into the second vessel 26 and the additional vessels when the orientation is in the first position. In other words, when the orientation is in the first position, the solution from the fluid sources 14, 16 may only be deposited into the first vessel 24. However, it is to be appreciated that when the orientation is in the first position, the sampling device 10 may be configured to permit ingress of the solution into the first vessel 24 and one or more additional vessels so long as the sampling device 10 is also configured to prevent ingress of the solution into the second vessel 26 when the orientation is in the first position (e.g., when duplicate samples are desired).

Figure 3B:
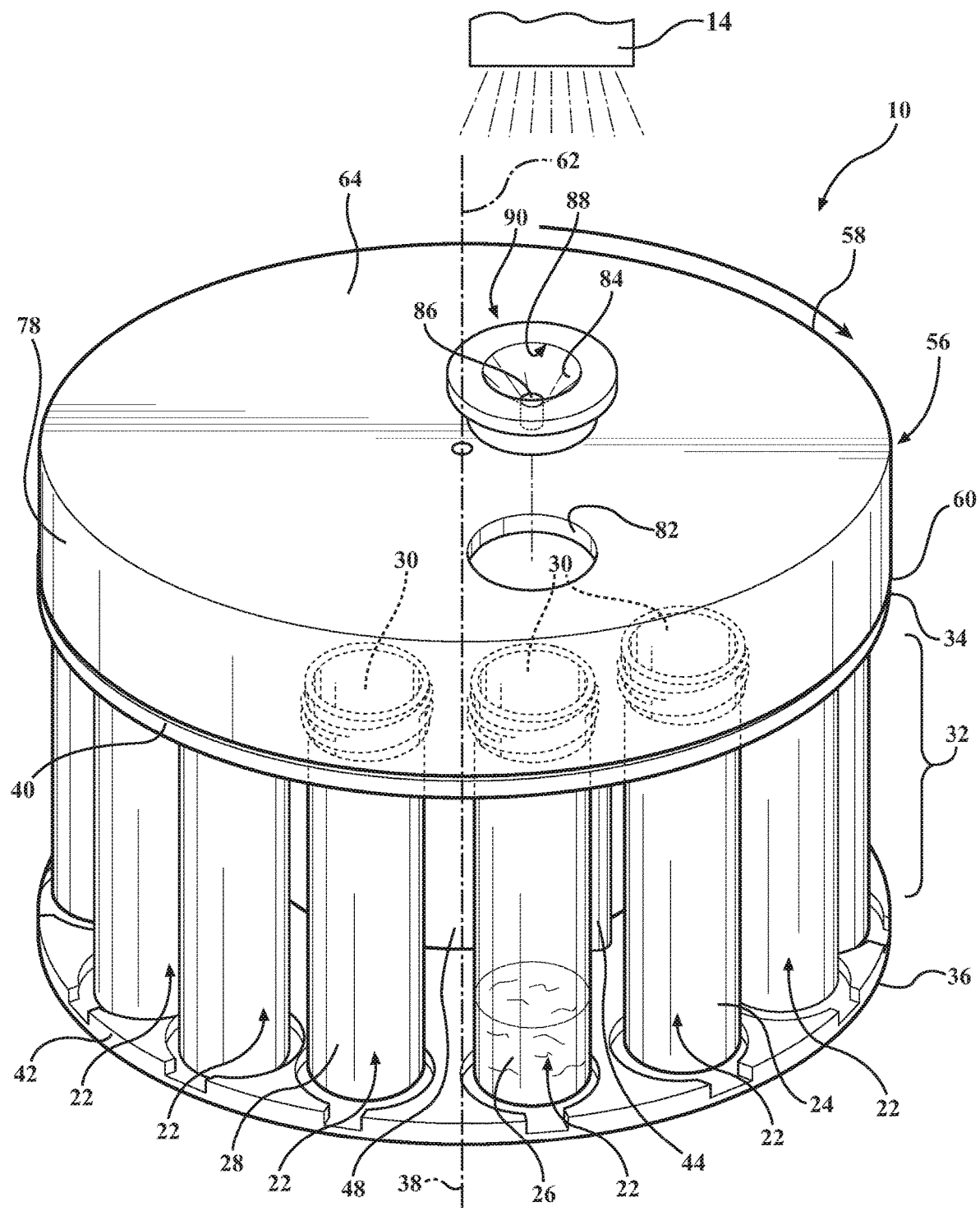
FIG. 3B is a perspective view of the sampling device in a second position.

Referring to FIG. 3B, the second position of the orientation of the sampling device 10 permits ingress of the solution through the orifice 82 into the second vessel 26. Thus, the orifice 82 permits fluid communication from the fluid sources 14, 16 to the second vessel 26 when the orientation is in the second position. More specifically, when the orientation is in the second position, the solution from the fluid sources 14, 16 may contact the outer portion 84 of the hole 88, move from the outer portion 84 to the inner portion 86 of the hole 88, move from the inner portion 86 to the opening 30 of the second vessel 26, and collect in the second vessel 26. In certain embodiments, the inner portion 86 of the hole 88 is inline with the opening 30 of the second vessel 26 such that the solution moves via gravity from the inner portion 86 to the opening 30 of the second vessel 26 when the orientation is in the second position.

When the orientation is in the second position, the cover 56 is configured to prevent ingress of the solution into the first vessel 24. In embodiments when the sampling device 10 includes additional vessels beyond the first vessel 24 and the second vessel 26, the cover 56 may be configured to prevent ingress of the solution into the first vessel 24 and the additional vessels when the orientation is in the second position. In other words, when the orientation is in the second position, the solution from the fluid sources 14, 16 may only be deposited into the second vessel 26. However, it is to be appreciated that when the orientation is in the second position, the sampling device 10 may be configured to permit ingress of the solution into the second vessel 26 and one or more additional vessels so long as the sampling device 10 is also configured to prevent ingress of the solution into the first vessel 24 when the orientation is in the second position (e.g., when duplicate samples are desired).

Figure 3C:
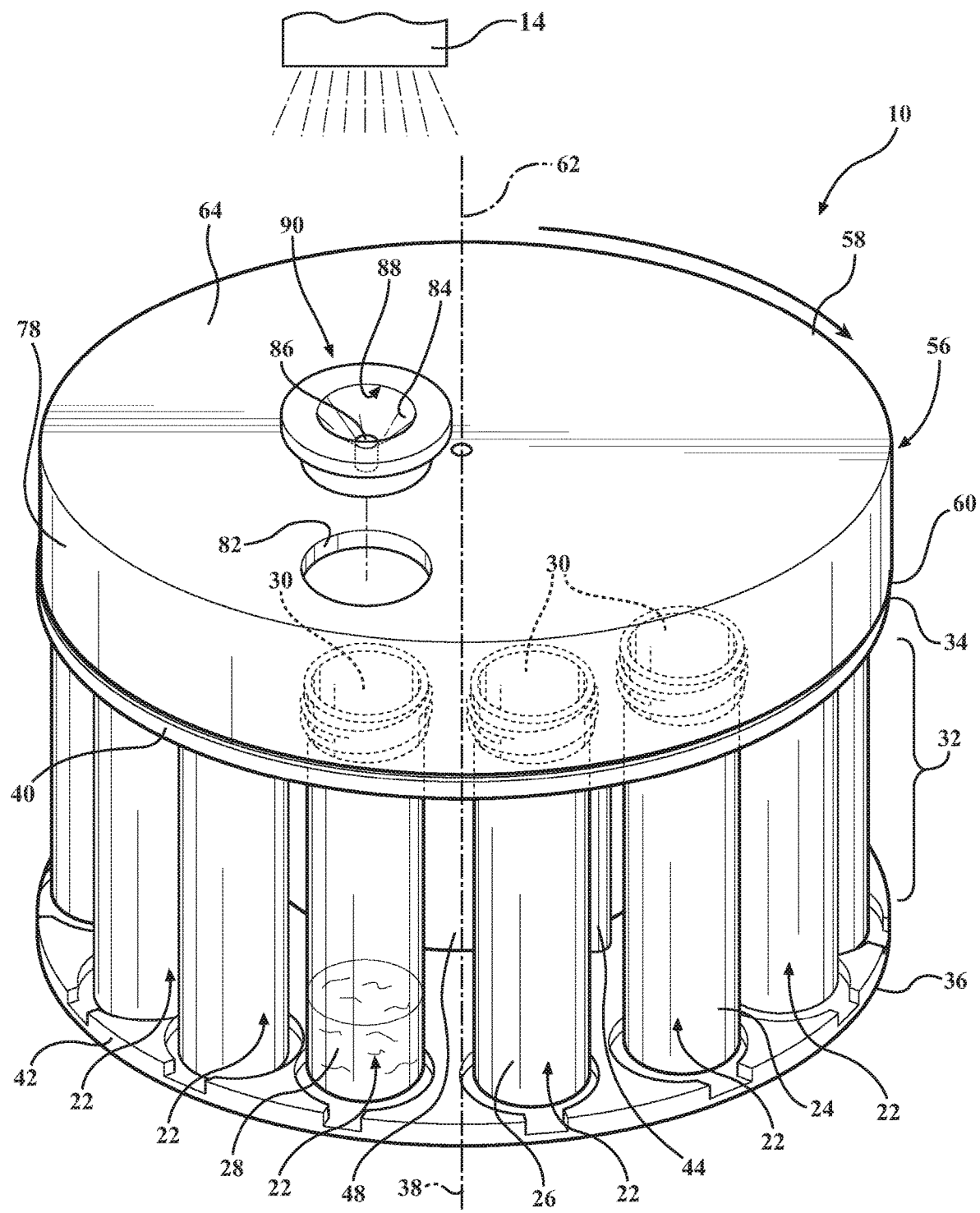
FIG. 3C is a perspective view of the sampling device in a third position.

Referring to FIG. 3C, the third position of the orientation of the sampling device 10 may permit ingress of the solution through the orifice 82 into the third vessel 28. Thus, the orifice 82 permits fluid communication from the fluid sources 14, 16 to the third vessel 28 when the orientation is in the third position. More specifically, when the orientation is in the third position, the solution from the fluid sources 14, 16 may contact the outer portion 84 of the hole 88, move from the outer portion 84 to the inner portion 86 of the hole 88, move from the inner portion 86 to the opening 30 of the third vessel 28, and collect in the third vessel 28. In certain embodiments, the inner portion 86 of the hole 88 is inline with the opening 30 of the third vessel 28 such that the solution moves via gravity from the inner portion 86 to the opening 30 of the third vessel 28 when the orientation is in the third position.

In embodiments when the orientation is in the third position, the cover 56 may be configured to prevent ingress of the solution into the first vessel 24 and the second vessel 26. In embodiments when the sampling device 10 includes additional vessels beyond the first vessel 24, the second vessel 26, and the third vessel 28, the cover 56 may be configured to prevent ingress of the solution into the first vessel 24, the second vessel 26, and the additional vessels when the cover 56 is in the third position. In other words, when the orientation is in the third position, the solution from the fluid sources 14, 16 may only be deposited into the third vessel 28. However, it is to be appreciated that when the orientation is in the third position, the sampling device 10 may be configured to permit ingress of the solution into the third vessel 28, either the first vessel 24 or the second vessel 26, and one or more additional vessels so long as the sampling device 10 is also configured to prevent ingress of the solution into either the first vessel 24 or the second vessel 26 when the orientation is in the third position (e.g., when duplicate samples are desired).

In certain embodiments, the cover 56 is movable relative to the vessels 22. In these embodiments, the vessels 22 may be in a fixed position and the cover 56 may move relative to the vessels 22. In one embodiment, the cover 56 rotates about the vessels 22. In another embodiment, the cover 56 moves transversely along the vessels 22. Of course, any suitable movement of the cover 56 relative to the vessels 22 is contemplated.

In embodiments when the cover 56 is movable relative to vessels 22, the cover 56 is movable to the first position and the second position. However, it is to be appreciated that the cover 56 may be moveable to the third position, with each of the positions corresponding to one of the vessels 22. In one embodiment, the cover 56 is movable to fifteen positions.

In certain embodiments, the motor 48 is configured to rotate the cover 56 about the first longitudinal axis 38 of the base 32 to the first position and to the second position. However, it is to be appreciated that the motor 48 may be configured to rotate the cover 56 to additional positions beyond the first position and the second position. Further, it is to be appreciated that the motor 48 may be configured to rotate the vessels 22 about the first longitudinal axis 48 of the base 32 to the first position and to the second position.

In other embodiments, the vessels 22 are movable relative to cover 56. In these embodiments, the cover 56 may be in a fixed position and the vessels 22 may move relative to the cover 56. In one embodiment, the vessels 22 rotates about the cover 56. In another embodiment, the vessels 22 moves transversely along the cover 56. Of course, any suitable movement of the vessels 22 relative to the cover 56 is contemplated.

Figure 9:
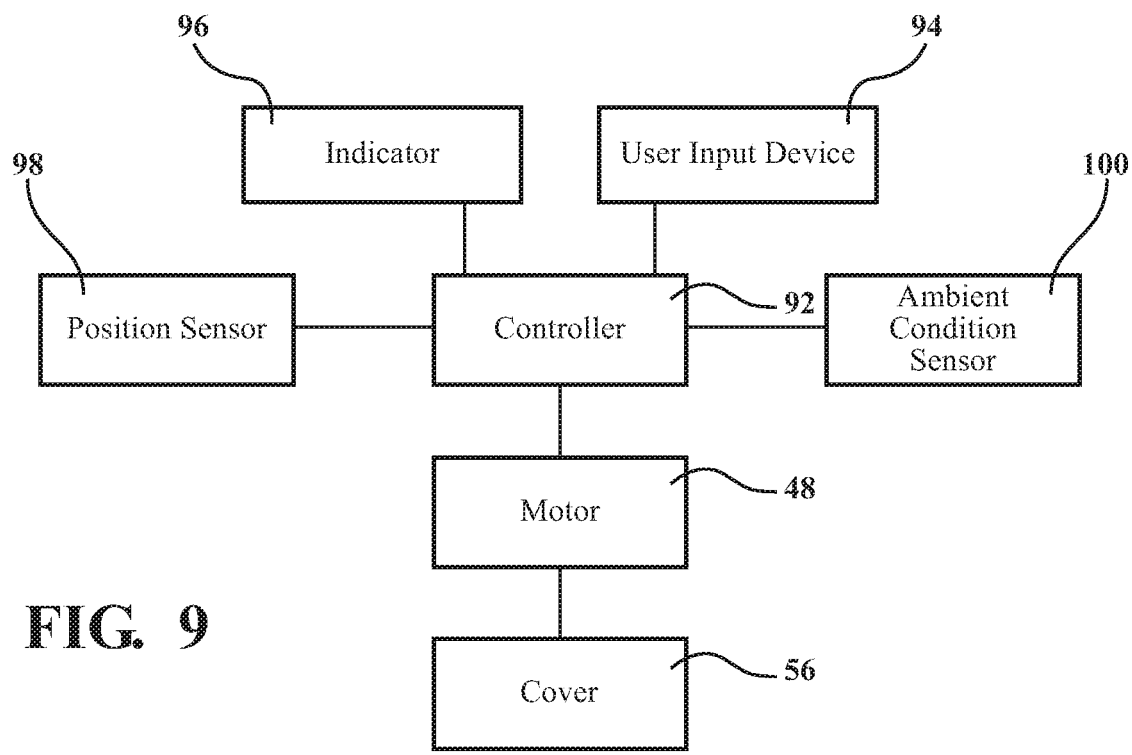
FIG. 9 is a schematic diagram of the sampling device of FIG. 1.

Referring to FIG. 9, the sampling device 10 may further include a controller 92 operatively coupled to the motor 48. In one embodiment, the controller 92 is configured to generate an output signal to drive the motor 48 to rotate to move the cover 56 from the first position to the second position in a predetermined duration. However, it is to be appreciated that the controller 92 may be configured to generate the output signal to drive the motor 48 to rotate to move the cover 56 from and to additional positions beyond the first position and the second position in the predetermined duration. The controller 92 may generate the output signal to drive the motor 48 to rotate to move the cover 56 from the first position to the second position in the predetermined duration of from 1 second to 24 hours, from 1 minute to 1 hour, or from 1 minute to 10 minutes. In one embodiment, the predetermined duration for the motor 48 to rotate to move the cover 56 from the first position to the second position is 5 minutes. In another embodiment, the predetermined duration for the motor 48 to rotate to move the cover 56 from the first position to the second position is 2.5 minutes. The predetermined duration may include a predetermined distance for the motor 48 to rotate to move the cover 56. In certain embodiments, the predetermined distance is further defined as an angular distance. The angular distance for the motor 48 to rotate to move the cover 56 from the first position to the second position may be from 10 to 360, from 15 to 100, or from 20 to 30, degrees. In one embodiment, the angular distance for the motor 48 to rotate to move the cover 56 from the first position to the second position is 24 degrees. These distances and durations are not limiting and may be correlated to the expected durations of the cycles of the medical sterilization device 12.

The controller 92 may be configured to generate the output signal to drive the motor 48 to rotate to move the cover 56 to one or more positions in one or more predetermined durations. For example, movement from the first position to the second position may be in a first predetermined duration, and movement from the second position to the third position may be in a second predetermined duration different from the first predetermined duration. In other words, the speed at which the motor 48 moves the cover 56 from the first position to the second position, may be different than the speed at which the motor 48 moves the cover 56 from the second position to the third position.

In another embodiment, the controller 92 is configured to generate the output signal to drive the motor 48 to rotate to move the cover 56 from the first position to the second position after the predetermined duration. However, it is to be appreciated that the controller 92 may be configured to generate the output signal to drive the motor 48 to rotate to move the cover 56 from and to additional positions beyond the first position and the second position after a predetermined duration. The controller may be located anywhere suitable to be operatively coupled to the motor 48. In one embodiment, the controller 92 is located on the motor 48.

The controller 92 may be configured to generate the output signal to drive the motor 48 to rotate to move the cover 56 to one or more positions after one or more predetermined durations. For example, movement of the cover 56 from the first position to the second position may be after a first predetermined duration, and movement of the cover 56 from the second position to the third position may be after a second predetermined duration different from the first predetermined duration.

The controller 92 may be configured to end generation of the output signal and thereby cease further driving of the motor 48 to rotate the cover 56. The end of generation of the output signal may be after the predetermined duration, or after the predetermined distance. As one example, in embodiments when the sampling device 10 includes fifteen vessels, the controller 92 may end generation of the output signal after the predetermined duration for movement of the cover 56 from the fourteenth position to the fifteenth position. As another example, in embodiments when the sampling device 10 includes fifteen vessels, the controller 92 may end generation of the output signal after the predetermined duration for movement of the cover 56 from the seventh position to the eight position. In other words, the controller 92 may prevent the sampling device 10 from assuming the first position a second time.

The step of changing the orientation of the cover 56 relative to the vessels 22 to the first position, the second position, or the third position may be further defined as the step of transmitting the output signal to the motor 48 to move the cover 56 to the first position, second position, or the third position to permit ingress of the solution through the orifice 82 into the first vessel 24, the second vessel 26, or the third vessel 28 and prevent ingress of the solution into the other vessels. However, it is to be appreciated that the vessels 22 may move to the first position, the second position, or the third position to permit ingress of the solution through the orifice 82 into the first vessel 24, the second vessel 26, or the third vessel 28 and prevent ingress of the solution into the other vessels.

The sampling device 10 may further include a user input device 94 coupled to the controller 92. A user may actuate the user input device 94 to transmit a corresponding user input signal to the controller 92. The controller 92, based on the user input signal received, may determine the predetermined duration for the motor 48. Furthermore, as described above, the controller 92 may transmit the output signal to drive the motor 48 in accordance with the predetermined duration. The user can select the predetermined duration to drive the motor 48, the predetermined speed to drive the motor 48, or a combination thereof. The user input device 94 may be located anywhere suitable to permit input from the user. In one embodiment, the user input device 94 is located on the motor 48. It is to be appreciated that the user input device 94 may be physically coupled to the controller 92 or wirelessly coupled to the controller 92.

The sampling device 10 may further include an indicator 96, and be configured to indicate the predetermined duration, the predetermined speed, or a combination thereof. The indicator 96 may include indicia such as text, graphics, lights, sound, vibration, etc. to indicate the predetermined duration, the predetermined speed, or a combination thereof. The indicator 96 may be located anywhere suitable to indicate information to the user. In one embodiment, the indicator 96 is located on the motor 48. It is to be appreciated that the indicator 96 may be physically coupled to the controller 92 or wirelessly coupled to the controller 92.

The sampling device 10 may further include a position sensor 98 in communication with the controller 92. The position sensor 98 is configured to sense the position of the sampling device 10. More specifically, the position sensor 98 may be configured to sense the position of the cover 56 relative to the base 32. Thus, the position sensor 98 may enable the controller 92 to determine whether the sampling device 10 is in the first position, the second position, and so forth. The position sensor 98 provides a position input signal to the controller 92.

The position sensor 98 may be located anywhere suitable to permit sensing of the position of the sampling device 10. In one embodiment, the position sensor 98 is located on the rack 40 of the base 32 of the sampling device 10. It is to be appreciated that the position sensor 98 may be physically coupled to the controller 92 or wirelessly coupled to the controller 92.

In one embodiment, the position sensor 98 includes one or more sensors for sensing the position of the sampling device 10. The type of position sensor is not particularly limited, and may include an optical sensor, a camera, a potentiometer, an encoder, or combinations thereof.

The sampling device 10 may further include an ambient condition sensor 100. The ambient condition sensor 100 is configured to sense an ambient condition of an environment of the tub 18, an environment of the sampling device 10, or a combination thereof. The ambient condition sensor 100 provides an ambient condition input signal to the controller 92. In certain embodiments, the indicator 96 is configured to indicate the ambient condition based on the ambient condition input signal provided by the ambient condition sensor 100.

The ambient condition sensor 100 may sense the ambient condition over time such that the sensed ambient conditions may be correlated with the solution gathered in the first vessel, second vessel, etc. Accordingly, in certain configurations, the ambient condition sensor 100 may sense the one or more ambient conditions at intervals that align with the duration when the sampling device 10 is in the first position, second position, etc.

In one embodiment, the ambient condition sensor 100 includes one or more sensors. The type of environmental sensor is not particularly limited, and may include a thermometer, a hygrometer, a barometer, or combinations thereof. The ambient condition sensor 100 may be used to determine a variety of ambient conditions in the environment of the tub 18, the environment of the sampling device 10, or a combination thereof, such as temperature, humidity, pressure, etc.

The ambient condition sensor 100 may be located anywhere suitable to permit sensing of the ambient condition of the environment of the tub 18, the environment of the sampling device 10, or a combination thereof. In one embodiment, the ambient condition sensor 100 is located on the bottom surface 66 of the cover 56 of the sampling device 10. It is to be appreciated that the ambient condition sensor 100 may be physically coupled to the controller 92 or wirelessly coupled to the controller 92.

Figure 8:
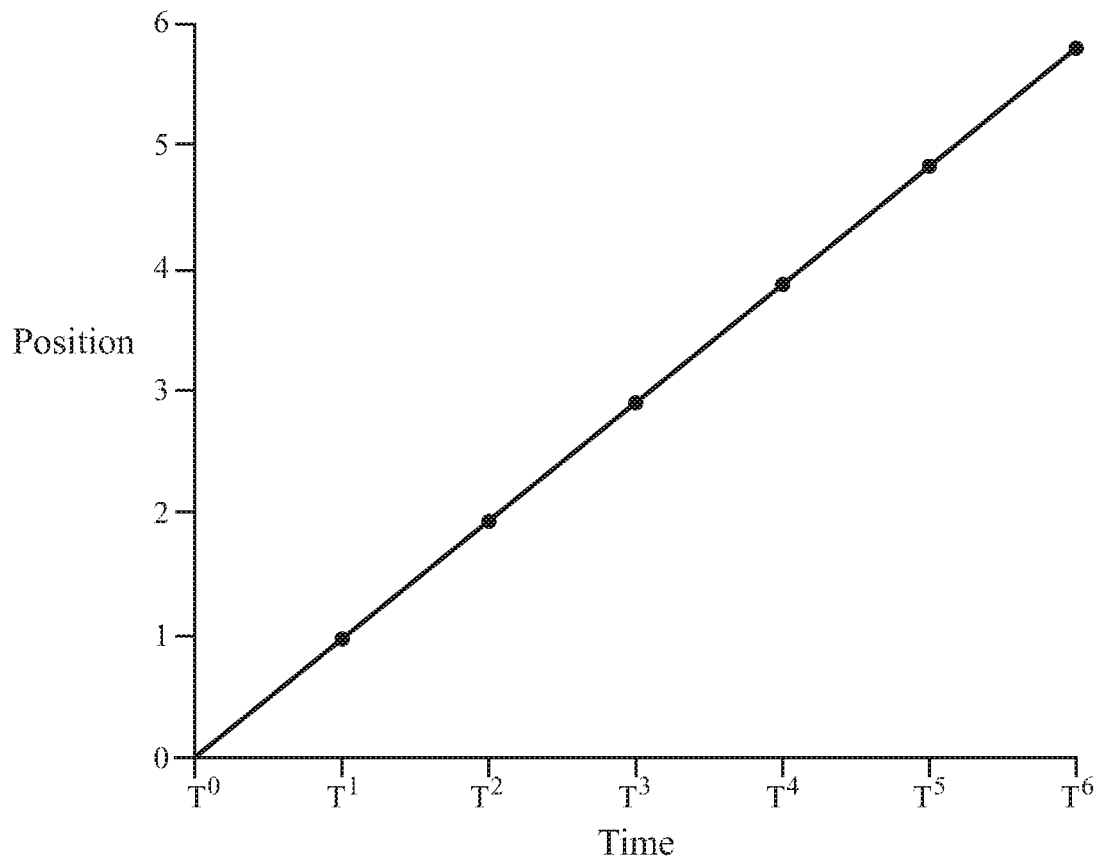
FIG. 8 is a graphical representation of various positions of the sampling device over a predetermined duration.

Referring to FIG. 8, the sampling device 10 may be configured to collect the plurality of samples of the solution in the vessels 22 in the predetermined duration. As one exemplary embodiment, the sampling device 10 may be configured to collect six samples of the solution in the predetermined duration of time points $T^0$ to $T^6$ based on the cycles of the medical sterilization device 12. The sample of solution at each of the time points is representative of a specific composition and concentration of the solution in the tub 18 of the medical sterilization device 12 at the time point. More specifically, $T^0$ to $T^1$ may represent the pre-wash cycle, $T^1$ to $T^2$ may represent the enzyme cycle, $T^2$ to $T^3$ may represent the wash cycle, $T^3$ to $T^4$ may represent the thermal rinse cycle, $T^4$ to $T^5$ may represent the rinse cycle, and $T^5$ to $T^6$ may represent the lubricant cycle. The user may select a duration and speed on the user input device 94 to direct the motor 48 of sampling device 10 to move the cover 56 to the first position at $T^1$, the second position at $T^2$, the third position at $T^3$, a fourth position at $T^4$, a fifth position at $T^5$, and a sixth position at $T^6$. It is to be appreciated that each time point may include more than one position of the cover 56 and thus each time point may include more than one sample. It is also to be appreciated that a single position may encompass more than one time point and thus one sample may encompass more than one time point.

The method may further include the step of analyzing the first sample to determine one or more analytical characteristics. The method may further include the step of analyzing the second sample to determine one or more analytical characteristics. The analysis to determine one or more analytical characteristics of the first sample and the second sample may be the same or different. It is to be appreciated the method may further include the step of analyzing the third sample. In one embodiment, the method may further include the step of analyzing fifteen samples.

The step of analyzing the samples may be conducted during the cycle of the medical sterilization device 12, after the cycle of the medical sterilization device 12, or a combination thereof. Through the use of one or more suitable analysis probes or sensors, which may be disposed in each of the vessels 22, the step of analyzing the samples may be conducted while the sampling device 10 is disposed in the tub 18 of the medical sterilization device 12 or after the sampling device 10 is removed from the tub 18. In one embodiment, the samples are analyzed after the sampling device 10 is removed from the tub 18.

The analytical characteristics may be analyzed utilizing gas chromatography ("GC"), gas chromatography-mass spectrometry ("GC-MS"), high performance liquid chromatography ("HPLC"), liquid chromatography-mass spectrometry ("LC-MS"), liquid chromatography-time-of-flight ("LC-TOF"), liquid chromatography-time-of-flight-mass spectrometry ("LC-TOF-MS"), mass spectrometry ("MS"), inductively coupled plasma-mass spectrometry ("ICP-MS"), atomic emission spectroscopy ("AES"), inductively coupled plasma atomic emission spectroscopy ("ICP-AES"), atomic absorption spectroscopy ("AAS"), UV-vis spectroscopy, IR spectroscopy, nuclear magnetic resonance spectroscopy ("NMR"), x-ray fluorescence, titration, gravimetric analysis, electrophoresis, microscopy, microelectromechanical systems chip, or combinations thereof.

The analytical characteristic may be selected from the group consisting of pH, total organic carbon ("TOC"), hardness, total dissolved solids ("TDS"), conductivity, salinity, detergent concentration, enzyme concentration, lubricant concentration, and combinations thereof. Hardness may include an analysis for polyvalent cations such as magnesium, calcium, iron, manganese, and zinc.

In other embodiments, the analytical characteristic may be selected from the group consisting of water quality analysis, microbiology analysis, trace metal analysis, organic analysis, physical property analysis, ambient condition analysis, and combinations thereof. The water quality analysis may include the following analyses: acidity, alkalinity, anion scan, bicarbonate, BOD, bromide, carbonate, chloride, chlorine, COD, color, conductivity, corrosively, cyanide, EDTA, ferrous iron, fluoride, formaldehyde, hardness, hydrazine, lead, MBAS, nitrogen, odor, oil and grease, oxidant demand, oxygen, petroleum hydrocarbons, pH, phenolics, phosphorus, resistivity, saturation index, settleability, silica, sulfate, sulfide, sulfite/bisulfite, sulfur, temperature, total inorganic carbon ("TIC"), total organic carbon ("TOC"), turbidity, or combinations thereof.

The microbiology analysis may include the following analyses: total coliform bacteria, *E. coli* bacteria, fecal coliform bacteria, acid-producing bacteria, iron bacteria, *Pseudomonas* bacteria, *Salmonella* bacteria, sulfate-reducing bacteria, heterotrophic plate count, microbiological evaluation, microscopic examination, yeast and mold, or combinations thereof.

The trace metals analysis may include the following analyses: aluminum, antimony, arsenic, barium, beryllium, bismuth, boron, cadmium, calcium, chromium, cobalt, copper, gallium, iron, lead, lithium, magnesium, manganese, mercury, molybdenum, nickel, potassium, selenium, silver, sodium, strontium, sulfur, thallium, tin, titanium, vanadium, zinc, zirconium, or combinations thereof.

The organic analysis may include the following analyses: volatile aromatics, volatile halocarbons, polynuclear aromatics, base/neutral extractables, acid extractables, aromatic amines, benzidines, chlordane, chlorinated paraffins, EDB/DBCP, EDTA, chlorinated herbicides, pesticides, PCB, phthalate esters, formaldehyde, alcohols/glycols, total hydrocarbons, or combinations thereof.

The physical property analysis may include the following analyses: corrosively, density, DOT burn rate, DOT dangerous when wet, DOT oxidizer, flash point, total halogen, heat of combustion, ignitability, liquid release, solids, specific gravity, total viscosity, volatile contents, total water, or combinations thereof.

The ambient condition analysis may include the following analyses: temperature, humidity, pressure, dry-time or combinations thereof.

Figure 11:
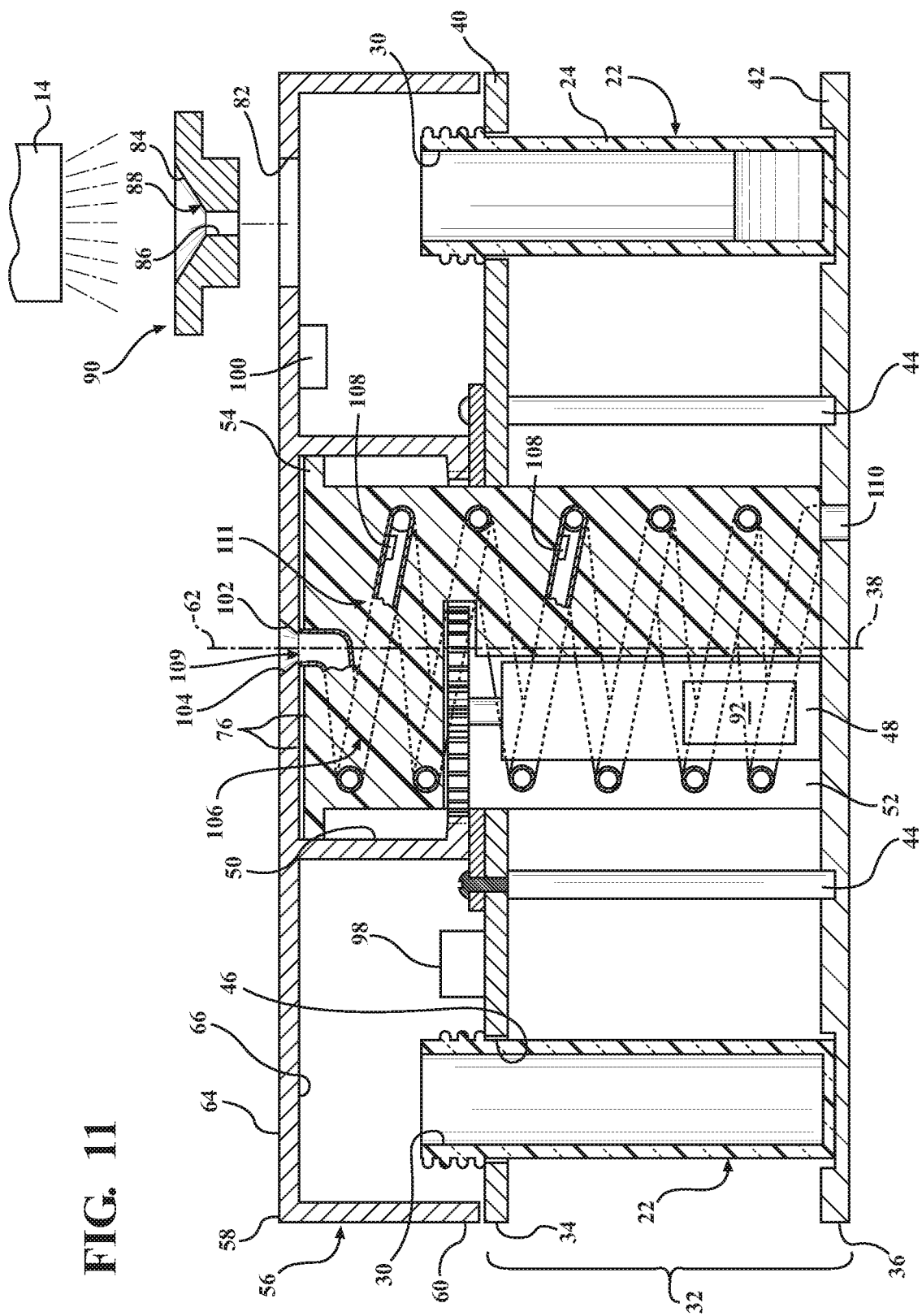
FIG. 11 is a cross-sectional view of the sampling device of FIG. 10 along line 11-11 showing a fluid path within the base and in communication with the openings, and the motor depicted schematically.

Referring to FIGS. 10 and 11, the sampling device 10 may be configured to receive solution in lieu of or in addition to the samples of the solution collected in vessels 22. The solution may be analyzed in real-time during the cycle of the medical sterilization device 12, after the cycle of the medical sterilization device 12, or a combination thereof. In certain embodiments, the solution is received through an opening 102 extending through the top surface 64 of the cover 56. The opening 102 may be coaxial with the first longitudinal axis 38. The opening 102 is exposed to or in fluid communication with the internal fluid source 14 of the medical sterilization device 12 such that a portion of the solution output from the internal fluid source 14 may pass through the opening 102. The base 32 may comprise an opening 104 aligned with the opening 102 of the cover 56 such that the opening 104 is in fluid communication with the internal fluid source 14 of the medical sterilization device 12. In one embodiment, the opening 104 is coaxial with the first longitudinal axis 38. The opening 104 may extend through the head 54 positioned above the housing 52 of the motor 48. The solution passing through the opening 102 of the cover 56 further passes through the opening 54 of the base 32.

The base 32 may comprise a fluid path 106. The fluid path 106 is in fluid communication with the opening 102 of the cover 56 and the opening 104 of the base 32. The fluid path 106 comprises and inlet 109 and an outlet 110. In certain embodiments, the inlet 109 of the fluid path 106 may be defined as the opening 102 of the cover 56 and/or the opening 104 of the base 32. The fluid path 106 is in fluid communication with the internal fluid source 14 of the medical sterilization device 12. The fluid path 106 is configured to receive the solution through the inlet 109.

The fluid path 106 may be disposed within the base 32 of the sampling device 10. In certain embodiments, the fluid path 106 may be disposed within an upper portion of the housing 52 of the motor 48. In the illustrative embodiment of FIG. 11, the base 32 comprises a core structure 111 discrete from the housing 52 of the motor 48. The core 111 may be positioned above the housing 52, but the reverse and other alternative configurations are contemplated. The fluid path 106 is disposed within the core 111.

The fluid path 106 of FIG. 11 is a helical fluid path within the core 111. Of course, other configurations of the fluid path 106 are contemplated, such as curvilinear, staircase, and zig-zag configurations. In certain embodiments, at least a portion of the fluid path 106 is non-vertical such that the solution is guided along the fluid path 106 in a generally controlled manner. In one embodiment, the fluid path 109 is tortuous to facilitate a generally steady flow of the solution within at least a portion of the fluid path 106. The fluid path 106 further comprises an outlet 110 in fluid communication with the inlet 109. The outlet 110 may extend through the floor 42 of the base 32 such that the solution passing through the outlet 110 drains within the tub 18 of the medical sterilization device 12 after passing through the outlet 110.

The base 32 comprises a sensor 108 within the fluid path 106. The sensor 108 may comprise one, two, or three or more sensors. The sensor 108 is positioned intermediate the inlet 109 and the outlet 110. In certain embodiments, the sensor 108 is positioned at a non-vertical portion of the fluid path 106 such that the sensor 108 senses the solution during the generally steady flow. In some embodiments, the sensor 108 is coupled to the base 32 adjacent or proximate to the fluid path 106. FIG. 11 shows the sensor 108 coupled to the core 111 at two portions of the helical fluid path. The sensor 108 is configured to determine one or more analytical characteristics of the solution as described throughout the present disclosure. In certain embodiments, the sensor 108 may comprise a thermocouple for determine temperature or hygrometer to determine humidity. Of course, other types of sensors are contemplated to determine any one or more of the analytical characteristics of the solution described throughout the present disclosure.

In certain embodiments, the sensor 108 determines the analytical characteristics in real-time during operation of the medical sterilization device 12. Whereas the samples of the solution collected in the vessels 22 are often analyzed subsequent to the operation of the medical sterilization device 12, determining the analytical characteristics during operation of the medical sterilization device 12 may provide real-time analysis and feedback. The real-time analysis may be provided at any predetermined number of time points, or upon actuation of the user input device 94. Referring to FIG. 8, the analytical characteristics may be analyzed at one or more time points for one more of the pre-wash cycle ($T^0$ to $T^1$), the enzyme cycle ($T^1$ to $T^2$), the wash cycle ($T^2$ to $T^3$), the thermal rinse cycle ($T^3$ to $T^4$), the rinse cycle ($T^4$ to $T^5$), and the lubricant cycle ($T^5$ to $T^6$). The analytical characteristics of the solution determined in real-time by the sensor 108 may substitute or supplement the analysis of the samples collected in the vessels 22.

Figure 13:
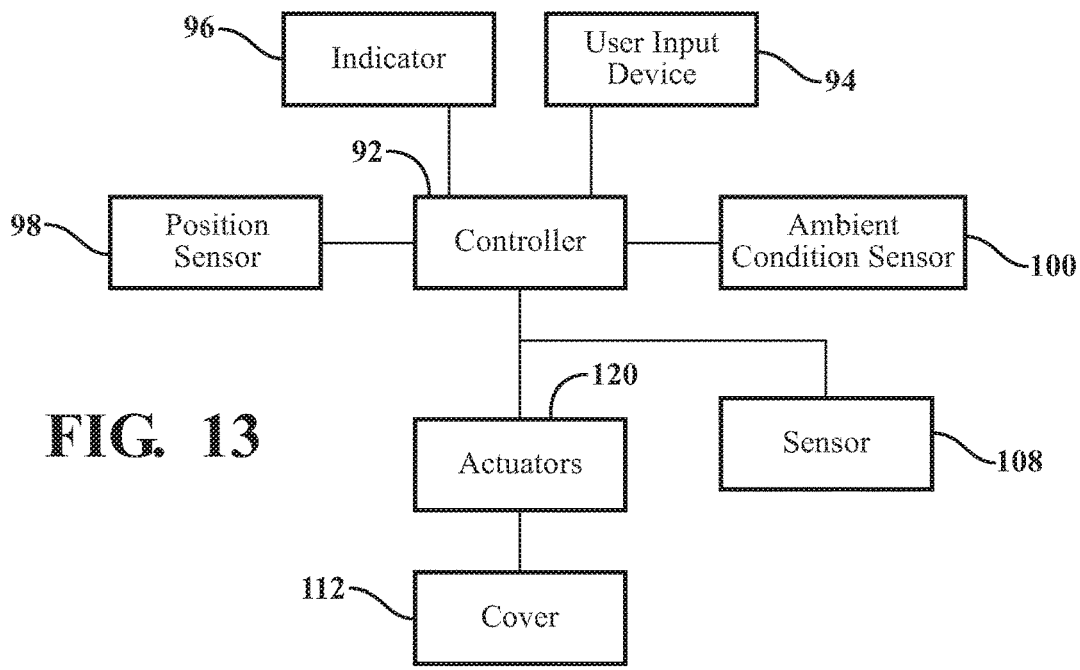
FIG. 13 is a schematic diagram of the sampling device of FIGS. 12A-12C.

The analytical characteristics of the solution determined in real-time by the sensor 108 may further be utilized to control the sampling device 10. Referring to FIG. 13, the controller 92 is in communication with the sensor 108. The controller 92 may be configured to generate the output signal to drive the motor 48 to rotate the cover 56 based on the analytical characteristics of the solution as determined by the sensor 108. In certain embodiments, the controller 92 generates the output signal to drive the motor 48 to rotate the cover 56 from the first position to the second position based on the analytical characteristics of the solution determined by the sensor 108. In one embodiment, the sensor 108 determines whether one of the analytical characteristics is outside expected or predefined limits. The sample of the solution is simultaneously being collected in one of the vessels 22, such as the first vessel 24, when the cover 56 is at the first position represented in FIG. 3A. To preserve the sample in its state (i.e., with the abnormal analytical characteristic) for subsequent, perhaps more rigorous analysis, the controller 92 generates the output signal to drive the motor 48 to rotate the cover 56 to the second position represented in FIG. 3B. In another embodiment, the sensor 108 determines a change in one or more of the analytical characteristics of the solution, with the change indicative of a switch between cycles of the medical sterilization device 12, such as from the pre-wash cycle to the enzyme cycle. In response to the change of the one or more of the analytical characteristics of the solution, the controller 92 generates the output signal to drive the motor 48 to rotate the cover 56 from the first position to the second position. Of course, other scenarios for rotating the cover 56 based on the analytical characteristics of the solution determined in real-time by the sensor 108 are contemplated.

Figure 12A:
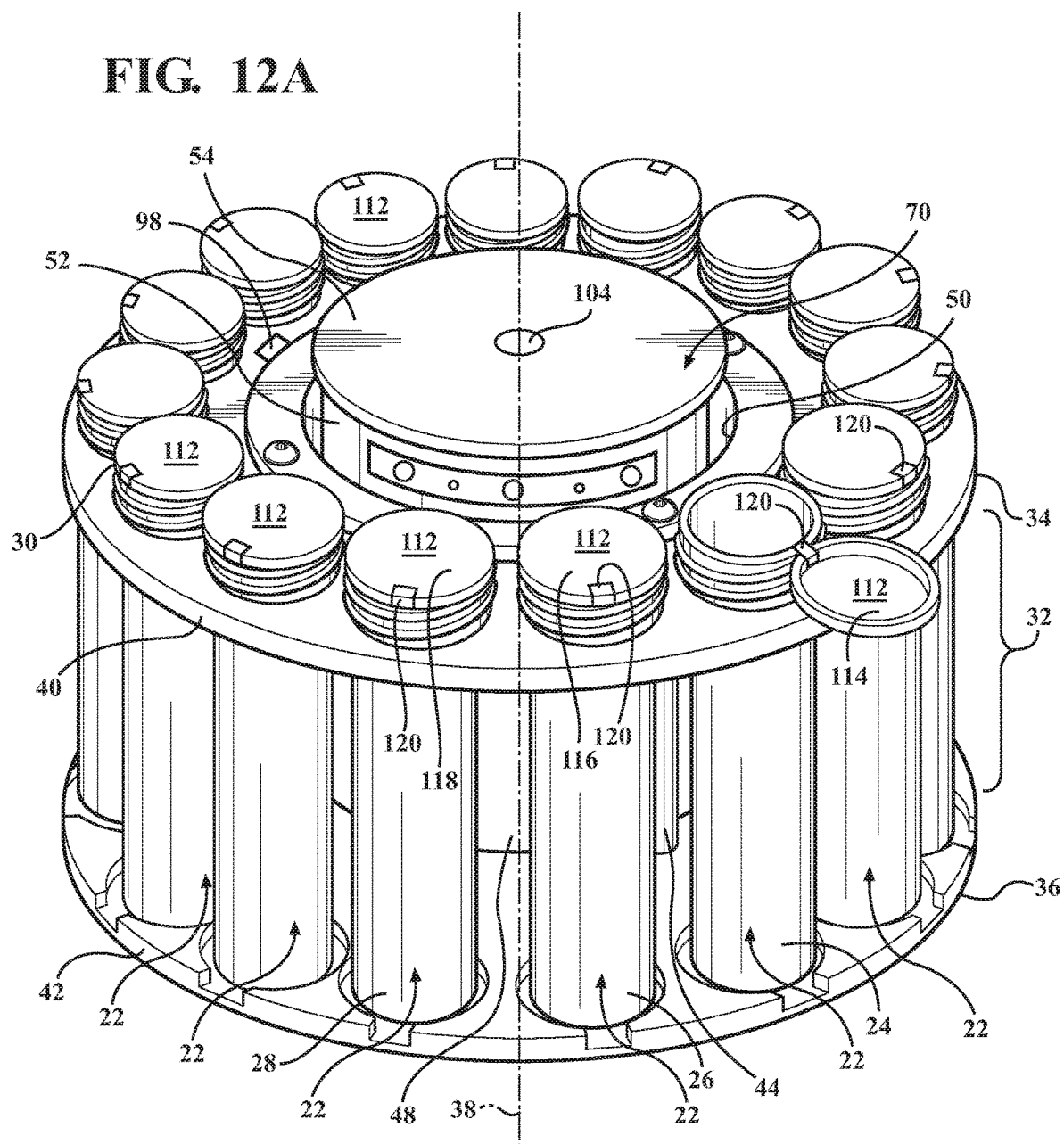
FIG. 12A is a perspective view of a sampling device in accordance with yet another exemplary embodiment with the sampling device in a first configuration.
Figure 12B:
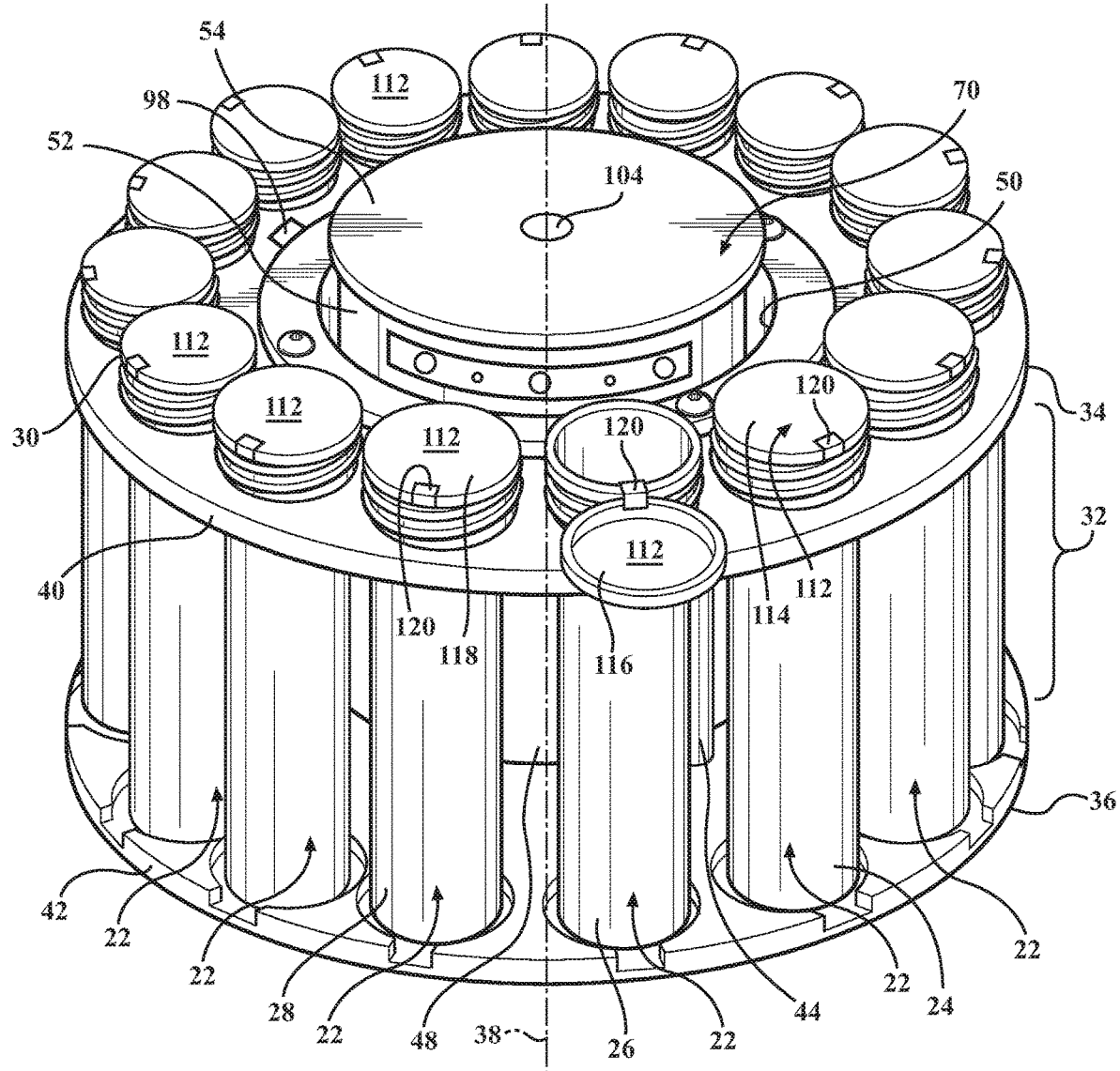
FIG. 12B is a perspective view of the sampling device of FIG. 12A in a second configuration.
Figure 12C:
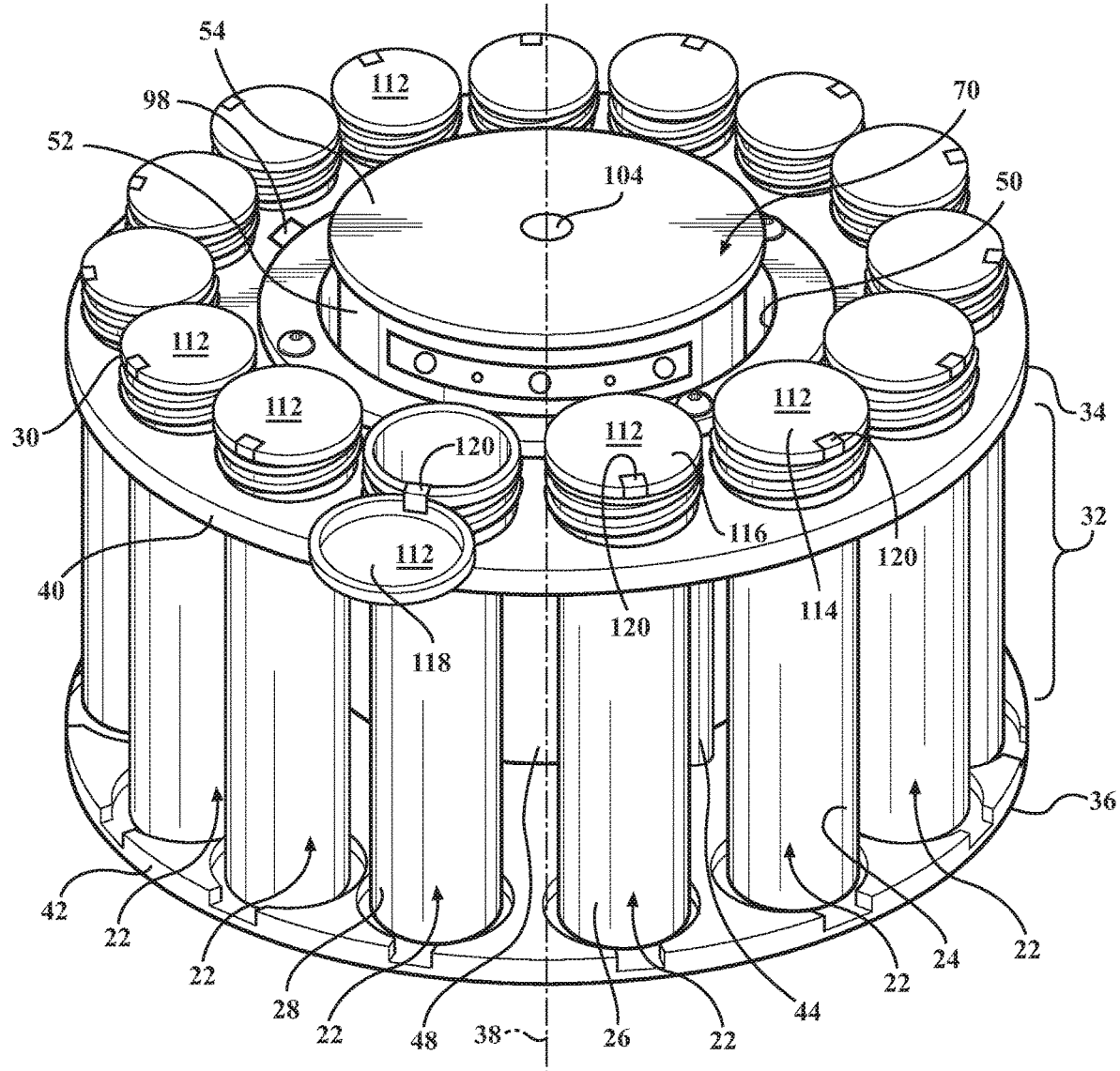
FIG. 12C is a perspective view of the sampling device of FIG. 12A in a third configuration.

FIGS. 12A-12C show the sampling device 10 in accordance with another exemplary embodiment of the present disclosure. The sampling device 10 includes the plurality of vessels 22 including the first vessel 24, the second vessel 26, and the third vessel 28. In one embodiment, the vessels 22 includes fifteen vessels. Non-limiting examples of the vessels 22 are described throughout the present disclosure. The sampling device 10 includes the base 32 configured to support the vessels 22 within the medical sterilization device 12. The base 32 has the top end 34 and the bottom end 36 with the first longitudinal axis 38 extending therebetween. The base 32 may include the rack 40 adjacent to the top end 34 and a floor 42 adjacent to the bottom end 36. The rack 40 may define the plurality of slots 46 with each of the slots 46 configured to removably accommodate one of the vessels 22. In various embodiments, when the vessels 22 are disposed in the rack 40, the openings 30 of the vessels 22 are disposed adjacent the top end 34 of the base 32. The base 32 may further include the pillars 44 disposed between the rack 40 and the floor 42. Both of the rack 40 and the floor 42 of the base 32 may extend transverse to the first longitudinal axis 38. The floor 42 of the base 32 may be disposed on the shelf of the tub 18 of the medical sterilization device 12.

Referring again to FIGS. 12A-12C, the sampling device 10 is deployable between a first configuration comprising permitting ingress of the solution into the first vessel 24 and preventing ingress of the solution into the second vessel 26, and a second configuration comprising preventing ingress of the solution into the second vessel 26 and permitting ingress of the solution into the first vessel 24. The sampling device 10 may be further deployable to a third configuration comprising permitting ingress of the solution into the third vessel 28 and preventing ingress of the solution into the first vessel 24 and the second vessel 26.

In certain embodiments, the sampling device 10 comprises a plurality of covers 112 with the covers 112 comprising a first cover 114, a second cover 116, and a third cover 118. In one embodiment, the covers 112 include fifteen covers. Each of the covers 112 may be coupled to one of the vessels 22. In one embodiment, the first cover 114 is coupled to the first vessel 24, the second cover 116 is coupled to the second vessel 26, and the third cover 118 is coupled to the third vessel 28. The sampling device 10 may comprise a plurality of actuators 120 each coupling one of the covers 112 with the corresponding one of the vessels 22. In one embodiment, the actuators 120 comprise fifteen actuators. FIGS. 12A-12C show a separate one of actuators 112 coupling the first cover 114 to the first vessel 24, the second cover 116 to the second vessel 26, and the third cover 118 to the third vessel 28. In one embodiment, the actuators 120 are servomotors configured to move the covers 112 relative to the vessels 22, such as by pivoting or sliding. For example, the covers 112 may each include a doorway that is opened by one of the actuators 120 to allow fluid ingress and/or the actuators 120 may lift the covers 112 relative to the vessels 22. Of course, other suitable mechanisms to impart relative movement between the covers 112 and the vessels 22 are contemplated.

The covers 112 are movable between a first position to permit ingress of the solution into the vessels 22, and a second position to prevent ingress of the solution into the vessels 22. In one embodiment, the first position may be such that the cover 112 is moved to expose at least a portion of the opening 30 of the vessel 22, and the second position may be such that the cover 112 is moved to prevent exposure of the opening 30 of the vessel 22.

FIG. 12A shows the sampling device 10 in the first configuration with the first vessel 24 configured to permit ingress of the solution and the second vessel 26 configured to prevent ingress of the solution. The first cover 114 is in the first position and the second cover 116 in the second position. In the first configuration, the third vessel 28 is configured to prevent ingress of the solution with the third cover 118 in the second position. In other words, in the first configuration, the solution from the fluid sources 14, 16 may be collected in only the first vessel 24.

FIG. 12B shows the sampling device 10 in the second configuration with the first vessel 24 configured to prevent ingress of the solution and the second vessel 26 configured to permit ingress of the solution. The first cover 114 is in the second position and the second cover 116 in the first position. In the second configuration, the third vessel 28 may prevent ingress of the solution with the third cover 118 in the second position. To deploy the sampling device 10 from the first configuration to the second configuration, one of the actuators 120 moves the first cover 114 from the first position to the second position, and another one of the actuators 120 moves the second cover 116 from the second position to the first position. In other words, in the second configuration, the solution from the fluid sources 14, 16 may collected only in the second vessel 26. In certain embodiments, the actuators 120 are configured to independently move the covers 122 between the first and second positions. In one embodiment, ingress of the solution is permitted into a singular one of the vessels 22 in both the first and second configurations.

FIG. 12C shows the sampling device 10 in the third configuration with the first vessel 24 configured to prevent ingress of the solution, the second vessel 26 configured to prevent ingress of the solution, and the third vessel 28 configured to permit ingress of the solution. The first cover 114 is in the second position, the second cover 116 in the second position, and the third cover 118 in the first position. To deploy the sampling device 10 from the first configuration to the third configuration, one of the actuators 120 moves the first cover 114 from the first position to the second position, another one of the actuators 120 moves the third cover from the second position to the first position. The second cover 116 remains in the second position. The sampling device 10 may be deployed from the second configuration to the third configuration. One of the actuators 120 moves the second cover 116 from the first position to the second position, and another one of the actuators 120 moves the third cover 118 from the second position to the first position. The first cover 114 remains in the second position. In other words, in the third configuration, the solution from the fluid sources 14, 16 may be collected only in the third vessel 28. In one embodiment, ingress of the solution is permitted into a singular one of said vessels 22 in both said first, second and third configurations. In other embodiments, ingress of the solution is permitted into more than one of the vessels 22 in the first, second and third configurations (e.g., when duplicate samples are desired).

Referring to FIG. 13, the sampling device 10 may further include the controller 92 operatively coupled to and/or in communication with the actuators 120. In one embodiment, the controller 92 is configured to generate an output signal to drive the actuators 120 to move the covers 112 between the first and second positions. In one embodiment, the controller 92 is configured to generate the output signal to drive the actuators 120 to move the covers 112 between the first and second positions in the predetermined duration (i.e., from 1 second to 24 hours, from 1 minute to 1 hour, or from 1 minute to 10 minutes, etc.). In certain embodiments, the predetermined duration may be the time elapsed between one of the actuators 120 moving one of the covers 112 between the first and second positions, and another one of the actuators 120 moving another one of the covers 112 between the first and second positions. These durations may be correlated to the expected durations of the cycles of the medical sterilization device 12. In various embodiments, deployment of the sampling device 10 from the first configuration to the second configuration may be in a first predetermined duration, and deployment from the second configuration to the third configuration may be in a second predetermined duration different from the first predetermined duration. In other words, the duration at which the sampling device 10 is in the first configuration may be different from the duration at which the sampling device 10 is in the second and/or third configurations.

Figure 7:
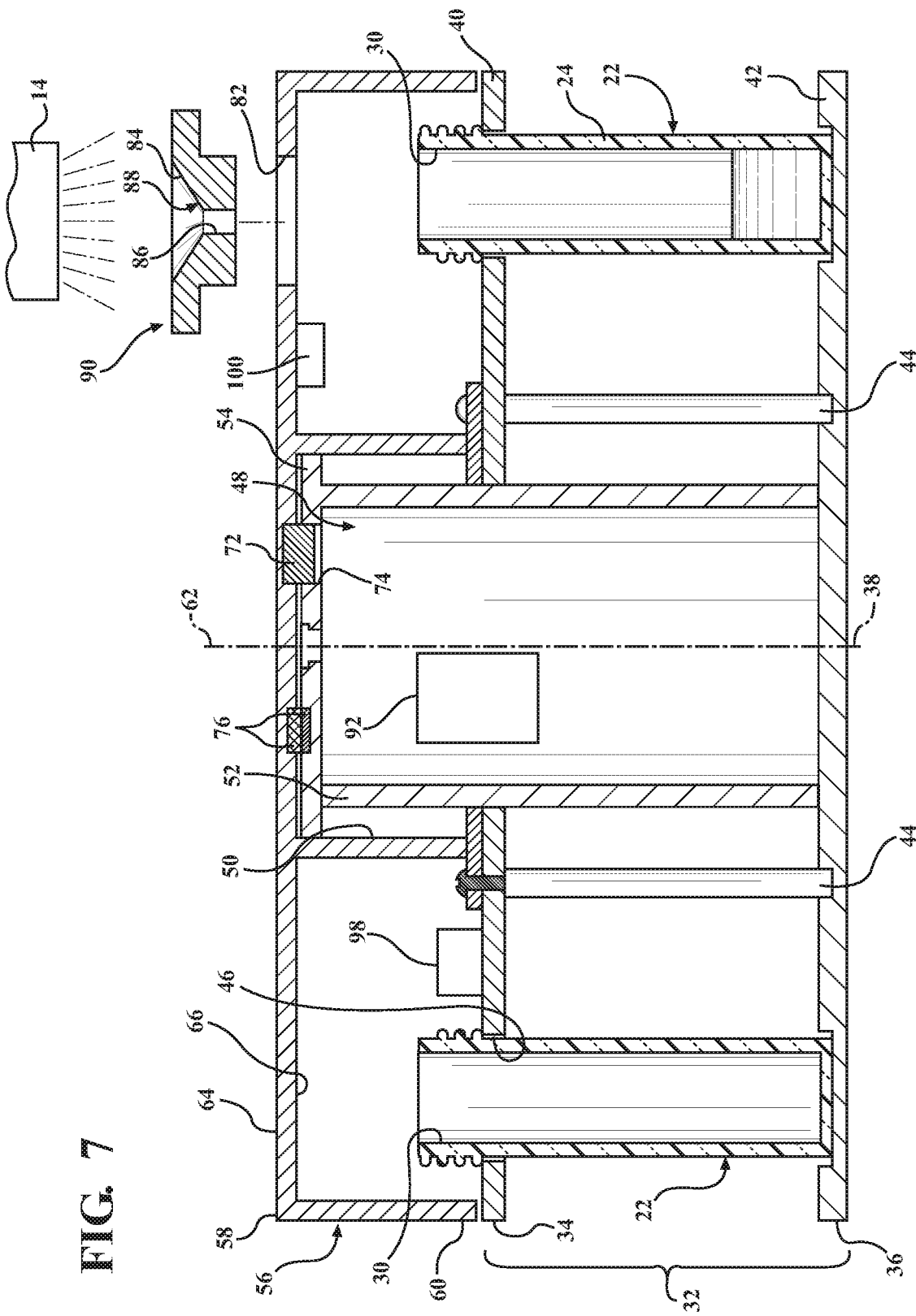
FIG. 7 is a cross-sectional view of the sampling device of FIG. 3A along line 7-7 with the motor depicted schematically.

The base 32 may further comprise the fluid path 106 in fluid communication with the internal fluid source 14 of the medical sterilization device 12, and the sensor 108 within the fluid path 106 intermediate the inlet 109 and the outlet 110. One non-limiting example of the structure and function of the fluid path 106 and the sensor 108 is disclosed in FIG. 7 and its corresponding description. FIGS. 12A-12C show the opening 104 within the base 32 that may define the inlet 109 for the fluid path 106.

The sensor 108 may determine the analytical characteristics in real-time during operation of the medical sterilization device 12. The real-time analysis may be provided at any predetermined number of time points, such as those shown in FIG. 8 and described herein, or upon actuation of the user input device 94. The analytical characteristics of the solution determined in real-time by the sensor 108 may be utilized to control the sampling device 10. Referring to FIG. 13, the controller 92 is in communication with the sensor 108 and the actuators 120. The controller 92 may generate the output signal to drive the actuators 120 to move the covers 112 coupled to the vessels 22 based on the analytical characteristics of the solution as determined by the sensor 108. In certain embodiments, the sensor 108 determines the analytical characteristics of the solution during operation of the medical sterilization device 12. The sampling device 10 is deployed to the first, second or third configurations based on the analytical characteristics of the solution. In one embodiment, the controller 92 generates the output signal in response to one of the analytical characteristics is outside normal limits. To preserve the sample being collected in one of the vessels 22, such as the first vessel 24, the controller 92 generates the output signal to drive one of the actuators 120 to move one of the covers 112, such as the first cover 114, from the first position to the second position, effectively preventing further ingress of the solution into the first vessel 24. The collected sample may undergo subsequent analysis. The controller 92 may further generate the output signal to drive another one of the actuators 120 to move another one of the covers 112, such as the second cover 116, from the second position to the first position, effectively permitting ingress of the solution into the second vessel 26. In another embodiment, the sensor 108 determines a change in one or more of the analytical characteristics of the solution during operation of the medical sterilization device 12. The change may be indicative of a switch between cycles of the medical sterilization device 12, such as from the pre-wash cycle to the enzyme cycle. In response to the change of the one or more of the analytical characteristics of the solution, the controller 92 generates the output signal to drive the actuators 120 to move one or more of the covers 112 between the first and second positions. Of course, other scenarios for actuating the covers 112 based on the analytical characteristics of the solution determined in real-time by the sensor 108 are contemplated.

Figure 14:
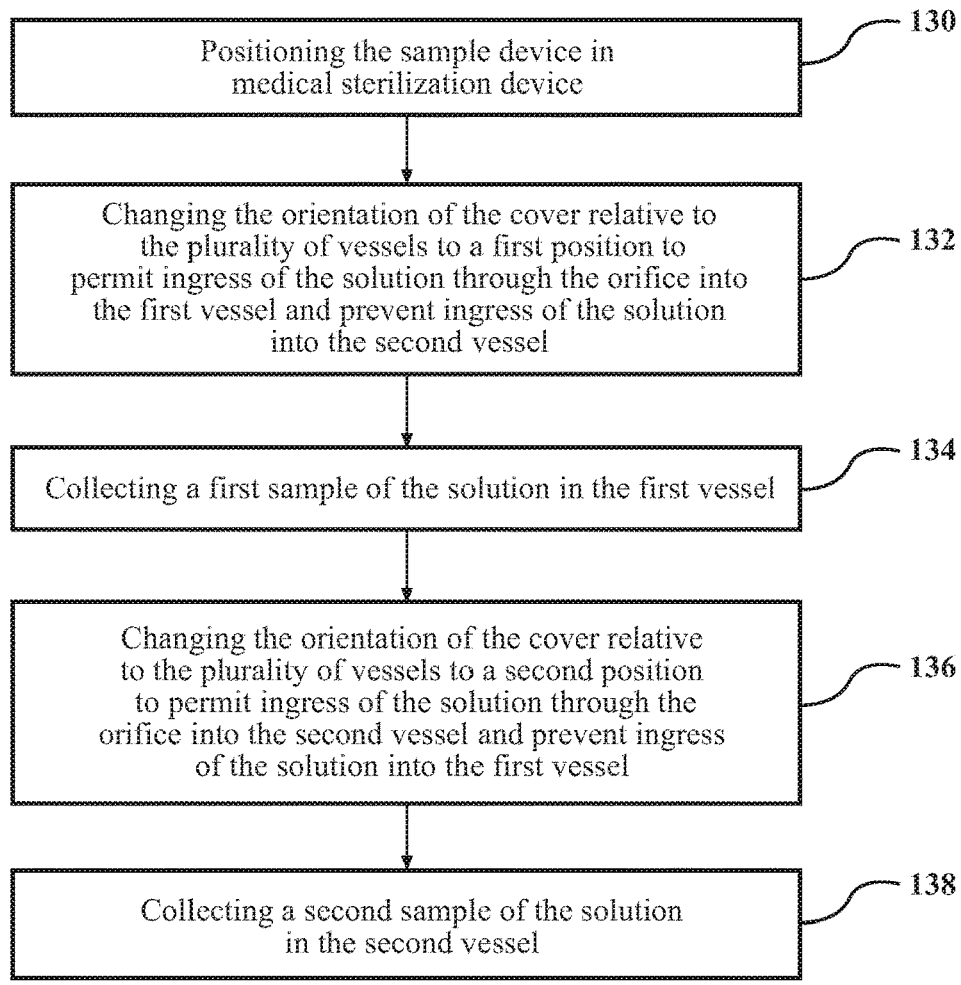
FIG. 14 is a schematic diagram of a method for collecting a plurality of samples utilizing the sampling device.

Referring to FIG. 14, an exemplary method includes: a step 130 of positioning the sampling device 10 in the medical sterilization device 12; a step 132 of changing the orientation of the cover 56 relative to the vessels 22 to the first position to permit ingress of the solution through the orifice 88 into the first vessel 24 and prevent ingress of the solution into the second vessel 26; a step 134 of collecting the first sample of the solution in the first vessel 24; a step 136 of changing the orientation of the cover 56 relative to the vessels 22 to the second position to permit ingress of the solution through the orifice 88 into the second vessel 26 and prevent ingress of the solution into the first vessel 24; and a step 138 of collecting the second sample of the solution in the second vessel 26.

Another exemplary method includes: a step of positioning the sampling device 10 in the medical sterilization device 12; a step of deploying the sampling device 10 in a first configuration to permit ingress of the solution into the first vessel 24 and prevent ingress of the solution into the second vessel 26; collecting a first sample of the solution in the first vessel 24; a step of deploying the sampling device 10 in a second configuration to prevent ingress of the solution into the first vessel 24 and permit ingress of the solution into the second vessel 26; and a step of collecting a second sample of the solution in the second vessel 26. The sampling device 10 may comprise a plurality of covers 112 having a first cover 114 movably coupled to the first vessel 24 and a second cover 116 movably coupled to the second vessel 26. The covers 112 are movable between a first position to permit ingress of the solution into the vessels 22 and a second position to prevent ingress of the solution into the vessels 22. Deploying the sampling device 10 in the first configuration may further comprise the step of moving the first cover 114 to the first position and the second cover 116 to the second position, and deploying the sampling device 10 in the second configuration may further comprise the step of moving the first cover 114 to the second position and the second cover 116 to the first position.

In certain embodiments, the methods includes a step of initiating a cycle of the medical sterilization device 12 such that the solution is circulated in the tub 18 from a fluid source 14 to the tub 18. The solution that is circulated in the tub 18 may be further defined as one or more circulated solutions.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method for analyzing a solution in a medical washing device in real-time, the method comprising the steps of:
   providing a sampling device with a fluid path having an inlet and an outlet;
   placing in the fluid path a sensor of an analytical characteristic wherein the analytical characteristic is at least one chosen from temperature, pH, salinity, total dissolved solids, and conductivity;
   positioning the sampling device in the medical washing device;
   initiating operation of the medical washing device;
   receiving the solution through the inlet of the fluid path with the inlet in communication with a source of the solution of the medical washing device;
   discharging the solution through the outlet of the fluid path; and
   determining in real-time the analytical characteristic of the solution with a signal provided by the sensor.

2. The method of claim 1, wherein the analytical characteristic includes each of temperature, pH, and conductivity.

3. The method of claim 2, wherein the analytical characteristic further includes at least one chosen from salinity, total organic carbon, hardness, detergent concentration, enzyme concentration, lubricant concentration, and combinations thereof.

4. The method of claim 1, further comprising the steps of:
   providing the sampling device with a controller; and
   placing the controller in communication with the sensor.

5. The method of claim 1, further comprising the steps of:
   providing the sampling device with a wireless coupling; and
   communicating the signal by the wireless coupling.

\* \* \* \* \*